(12) United States Patent
Becker

(10) Patent No.: US 10,595,876 B2
(45) Date of Patent: Mar. 24, 2020

(54) PUNCTAL PLUG INSERTER TOOL INCLUDING A PENETRATION-RESISTING BEARING SURFACE AND METHOD

(71) Applicant: Bruce B. Becker, Malibu, CA (US)

(72) Inventor: Bruce B. Becker, Malibu, CA (US)

( * ) Notice: Subject to any disclaimer, the term of this patent is extended or adjusted under 35 U.S.C. 154(b) by 291 days.

(21) Appl. No.: 15/494,283

(22) Filed: Apr. 21, 2017

(65) Prior Publication Data

US 2017/0224356 A1 Aug. 10, 2017

Related U.S. Application Data

(63) Continuation-in-part of application No. 14/664,604, filed on Mar. 20, 2015, now Pat. No. 10,406,028, which is a continuation-in-part of application No. 13/186,665, filed on Jul. 20, 2011, now Pat. No. 9,254,225.

(51) Int. Cl.
*A61B 17/00* (2006.01)
*A61B 17/12* (2006.01)
*A61F 9/007* (2006.01)

(52) U.S. Cl.
CPC .. *A61B 17/12159* (2013.01); *A61B 17/12031* (2013.01); *A61B 17/12099* (2013.01); *A61F 9/00772* (2013.01); *A61B 2017/00902* (2013.01); *A61B 2017/12054* (2013.01)

(58) Field of Classification Search
CPC .............. A61F 9/0017; A61F 9/00772; A61F 9/00781; A61B 17/12031; A61B 17/12099; A61B 17/12159; A61B 2017/00902; A61B 2017/12054
See application file for complete search history.

(56) References Cited

U.S. PATENT DOCUMENTS 3,949,750 A * 4/1976 Freeman ............... A61F 9/0017
424/427
6,527,780 B1 * 3/2003 Wallace ........... A61B 17/12022
606/1

OTHER PUBLICATIONS

Kaido, Minako, et al., A New Punctal Plug Insertion Technique to Prevent Intracanalicular Plug Migration, American Journal of Ophthalmology, vol. 147, No. 1 (pp. 178-182) Jan. 2009.

* cited by examiner

*Primary Examiner* — Benjamin J Klein
(74) *Attorney, Agent, or Firm* — Charmasson, Buchaca & Leach, LLP

(57) ABSTRACT

A surgical tool for inserting a spile or plug into the punctal opening of a meatus such as a lacrimo-nasal canaliculus. The tool includes a distal end having a plug-carrying structure which includes distally extending rod for engaging an axial bore in the plug, and an abutment having a radial prominence supporting a penetration-resisting bearing surface which prevents over-insertion of the plug by contacting tissue surrounding the punctal opening. The abutment can be shaped and dimensioned to provide effective and comfortable penetration resistance while affording ample visibility to the surgeon user. The rod can be axially withdrawn through a rod tracking tube having a precisely dimensioned central lumen restricting off-axis movement of the rod. The abutment can be fixed to the rod or detached from it.

26 Claims, 17 Drawing Sheets

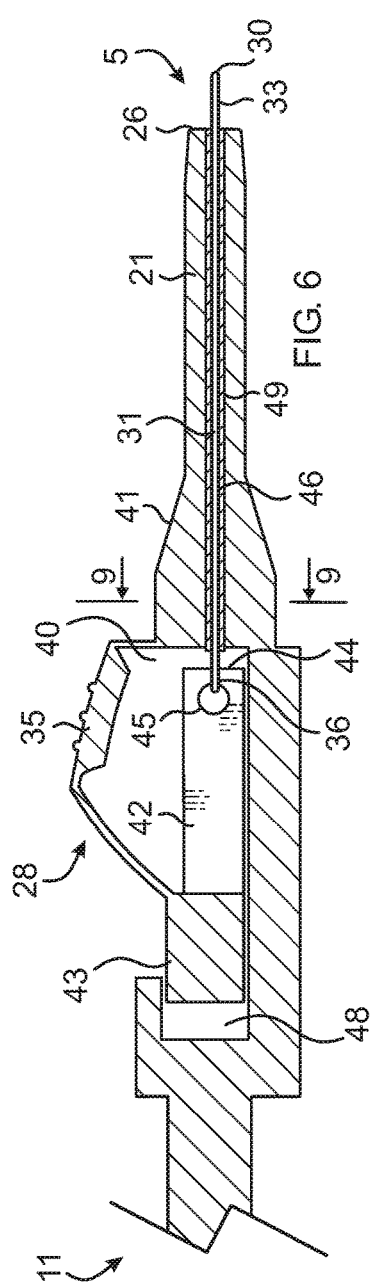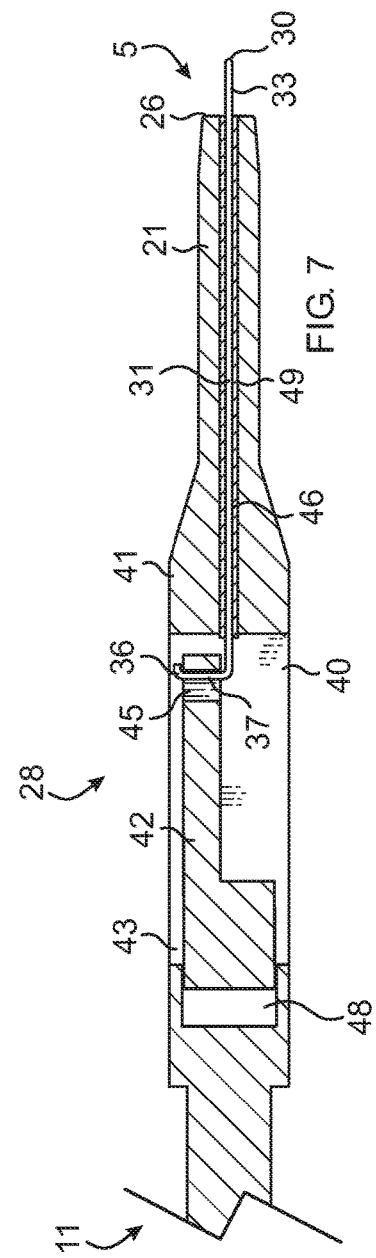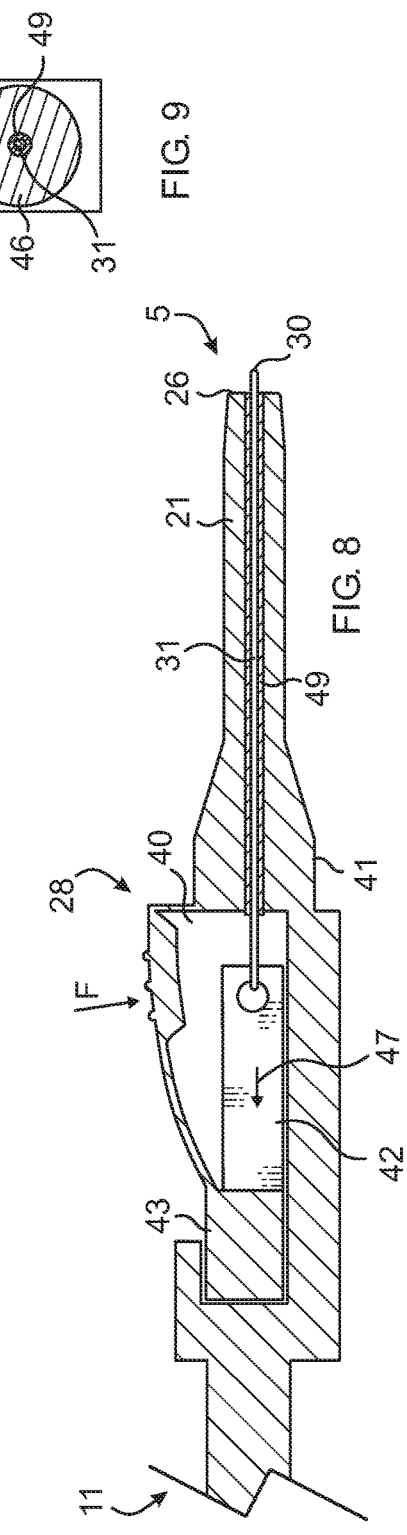

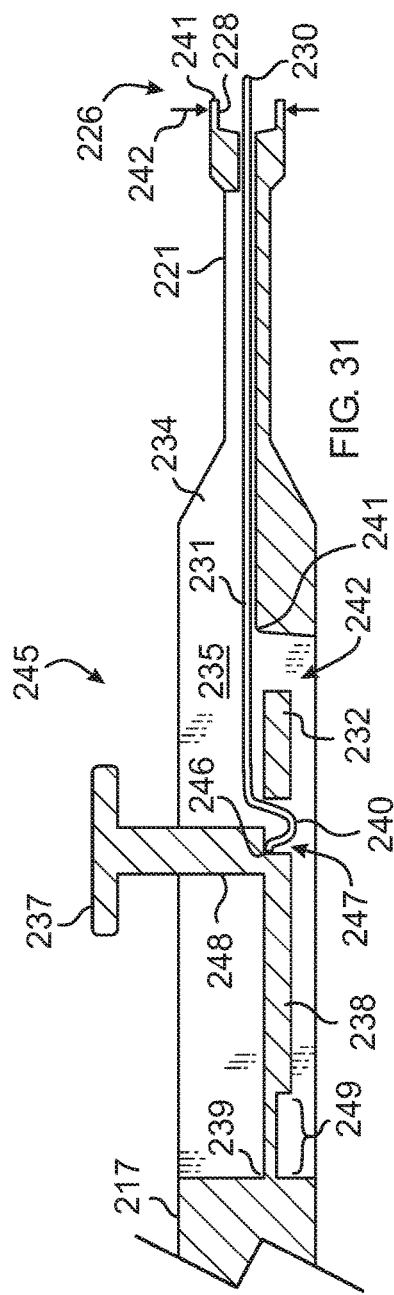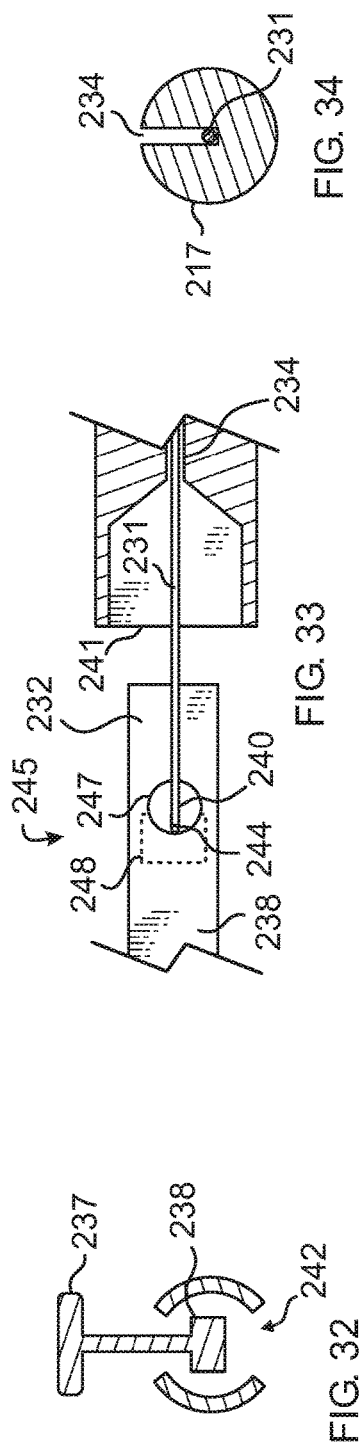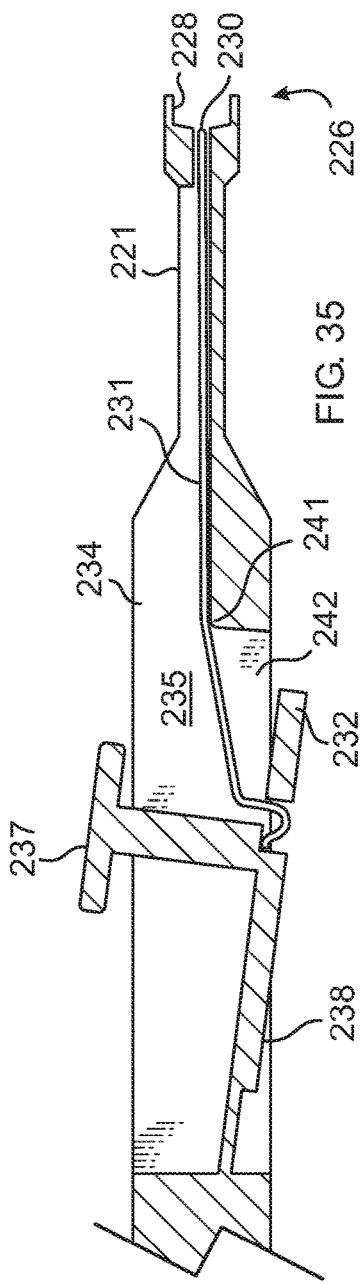

PUNCTAL PLUG INSERTER TOOL INCLUDING A PENETRATION-RESISTING BEARING SURFACE AND METHOD

PRIOR APPLICATION

This is a continuation-in-part of U.S. patent application Ser. No. 14/664,604, filed 2015 Mar. 20, which is a continuation-in-part of U.S. patent application Ser. No. 13/186,665, filed 2011 Jul. 20, now U.S. Pat. No. 9,254,225, issued 2016 Feb. 9, incorporated herein by reference.

FIELD OF THE INVENTION

This invention relates to surgical implements and more specifically to instruments used in the treatment and repair of meati, particularly naso-lacrimal canaliculi and puncta.

BACKGROUND

Dry eye syndrome which usually results from inadequate production of the aqueous layer of tears can often be palliated by obstructing the punctum that drain tears into the nose. This is done by means of minuscule punctal spiles or plugs. Each plug features a distal glanduliform or barbed head. The head acts as an anchor and is backed by a short median shank of a cross-diameter substantially smaller than the largest portion of the head, and a broad circular proximal cap which remains outside the punctum and can be seized with tweezers or pincers to extract the plug. The largest cross-diameter of the head must be slightly larger than the cross-diameter of the canaliculus and its opening punctum in order to maintain the plug in its optimal position.

The prior art offers an ophthalmic punctal opening dilatation and plug insertion tool available under the name Ready-Set Punctum Plug from FCI Opthalmics of Marshfield Hills, Massachusettes which consists of a pencil dimensioned member having at one end a dilating reamer and at the opposite end a thin shaft through which runs a small axially translatable rod. The distal extremity of the rod protrudes slightly from the end of the shaft and is sized to penetrate a small axial bore in the proximal face of the proximal cap and thus hold the plug during its insertion into the punctal opening of a canaliculus or other type of meatus. A bi-directional squeeze mechanism in the median portion of the tool withdraws the rod and releases the plug once it has reached the desired position.

The prior art tool suffers from several critical drawbacks.

First, the dilating reamer is constituted by circular shaft of a substantial cross-diameter terminated by an elongated conical spike. The degree of penetration of the spike into a meatus determines the amount of obtained dilation. Although such a dilator has the flexibility of providing an adjustable amount of dilatation, the physician can only estimate how far to push the dilator into the punctal opening. If the dilatation is not sufficient, the insertion of the plug may be painfully difficult or impossible. If the dilatation exceeds the diameter of the proximal cap, the plug may be inadvertently pushed too far into the canaliculus. If the dilatation even exceeds the largest diameter of the anchoring head, the plug may be too loose and soon exit the meatus.

Second, because of the relatively large forces typically required to insert the typically tight-fitting plug, it can be difficult for the physician to judge whether the force is the correct amount needed to seat the plug at the proper optimum depth with respect to the punctum. In other cases the force required to push the plug into the punctum carries the plug too deeply into the canaliculus. Plugs which have been inserted too deeply can be difficult to remove, leading to tissue damage, infections, tearing or other complications. Potentially exacerbating the problem is that the plugs are often made from a soft, flexible material such as silicone often having a durometer of 60 A which will tend to distort under the insertion forces, making it difficult to place the plug properly. The soft cap of the plug cannot prevent the plug from being placed too deeply through the punctum and into the canaliculus. Physicians are taught and follow the practice of pushing with the minimum force possible. However, as noted above, this force can be impossible to accurately judge given the variability inherent in the procedure. In many situations the force required to push the head through the punctal opening causes the entire plug to go too deep.

Third, the prior art bi-directional squeeze mechanism for retracting the rod is located on a part of the tool that the physician will typically need to grasp during insertion. Therefore, when the physician grasps this portion and applies force to the tool to insert the plug through the punctum, it is possible for the physician to inadvertently actuate the squeeze mechanism and prematurely release, or partially dislodge the plug from the tool. Further, because the squeeze mechanism typically requires that the physician's thumb and index finger be located on opposite sides of the mechanism in order to actuate withdrawal of the rod, control of the tool, especially under force is made difficult.

Fourth, in order to keep manufacturing costs low, the disposable body of the tool is often made of injection molded plastic to relatively low dimensional tolerances. During insertion, forces on the rod can cause the soft plug to move in an off-axis manner and buckle within its loose-fitting channel, potentially leading to inadvertent retraction and unintentional premature dislodgement of the plug from the tool.

In addition, the precarious holding of the plug by the small amount of the rod that penetrates the plug may not allow the physician much freedom of action during the insertion process, and often results in the inadvertent, premature separation of the sterile plug from the tool. The plug may be dropped before insertion or left only partially inserted. In the latter instance, another tool must be used to extract the partially inserted plug and re-attach it to the insertion tip in order to attempt a repeat of the insertion procedure. Such procedures can be difficult and time-consuming.

Many surgeons prefer to maximize visualization of the plug during insertion to the extent possible. Devices which seek to stabilize the plug while it is attached to the inserter can tend to obscure the view of the plug. This can lead to an undesirable tradeoff between stability and visibility.

Presently, many prior punctal plug insertion tools use a retractable rod. However, the surfaces guiding the rod allow the rod to bend or buckle as force is applied to the insertion tool during placement of the punctal plug into the punctum. This will then alter the distance between the body of the insertion tool and the plug, resulting in imprecise control over the plug.

Therefore, there is a need for a punctal plug insertion device and method which addresses one or more of the above problems.

SUMMARY

The principal and secondary objects of the invention are to provide improved treatment of meati.

These and other objects are achieved by a plug inserter tool having an penetration-resisting bearing surface to help prevent over-penetration of the plug into the meatus. In some embodiments there is provided a tool which includes a distally extending rod having at its distal end a plug-carrying structure including an abutment having a radial prominence supporting a penetration-resisting bearing surface which prevents over-insertion of the plug by contacting tissue surrounding the punctal opening. In some embodiments the abutment can be shaped and dimensioned to provide effective and comfortable penetration resistance while affording ample visibility to the surgeon user. In some embodiments, the rod can be axially withdrawn in a precisely controlled manner by unidirectionally pressing a button on the member.

In some embodiments there is provided the combination of a punctal plug and a tool for inserting said plug into the punctal opening of a meatus; wherein said plug comprises: a shank having a proximal end and a distal end; an insertable portion connected to said distal end; and, a proximal cap connected to said proximal end, said cap having a distal flange surface oriented to rest against at least part of the tissue surrounding said opening when said plug is properly emplaced in said meatus; wherein said tool comprises: a member having a distal portion, and a rod projecting from said distal portion; said rod having a distal segment elongated along an axis, said distal segment having a free distal rod end; an abutment located an axial distance from said distal rod end; wherein said abutment comprises: a penetration-resisting bearing surface located at an axial position to resist penetration of said distal flange surface through said punctal opening, thereby preventing over-penetration of said plug into said meatus.

In some embodiments said penetration-resisting bearing surface extends beyond a maximum radial extent of said shank.

In some embodiments said penetration-resisting bearing surface extends at least 0.1 mm beyond a maximum radial extent of said shank.

In some embodiments said penetration-resisting bearing surface extends beyond a maximum radial extent of said cap.

In some embodiments said penetration-resisting bearing surface extends at least 0.1 mm beyond a maximum radial extent of said cap.

In some embodiments said penetration-resisting bearing extends between about 0.1 mm and about 5.5 mm beyond a maximum radial extent of the shank of the plug being inserted.

In some embodiments said penetration-resisting bearing surface is dimensioned to bear directly or indirectly against at least part of the tissue surrounding said opening during insertion of said plug into said meatus.

In some embodiments a portion of said penetration-resisting bearing surface indirectly bears against a portion of tissue surrounding said opening through said proximal cap of said plug, whereby said distal flange surface and said insertion-resisting bearing surface combine to form a substantially continuous combined surface.

In some embodiments a portion of said penetration-resisting bearing surface forms a barrier to axially proximal movement of said cap, whereby said penetration-resisting bearing surface and said proximal cap form a penetration-resisting functional unit.

In some embodiments said abutment is substantially cylindrical and wherein said penetration-resisting bearing surface is substantially circular having a diameter of between about 0.91 mm and about 6.0 mm.

In some embodiments said abutment comprises a rounded radial periphery.

In some embodiments said abutment comprises a plurality of angularly spaced apart surface portions having a cumulative area forming said penetration-resisting bearing surface.

In some embodiments said abutment comprises at least one radial notch forming an angular discontinuity in said penetration-resisting bearing surface.

In some embodiments said abutment comprises a pane of translucent material.

In some embodiments said at least one radial notch extends angularly a first angle.

In some embodiments said abutment comprises at least one radial notch angularly adjacent to said radial prominence.

In some embodiments said at least one radial notch extends axially a first axial length.

In some embodiments said at least one radial notch extends distally to an extent to interrupt an angular gap in said bearing surface.

In some embodiments said abutment is fixed to said rod.

In some embodiments said abutment is axially positioned on said rod so that a proximal surface of said cap abuts against a part of said abutment during insertion of said plug into said meatus.

In some embodiments said penetration-resisting bearing surface and said distal flange surface are substantially coplanar.

In some embodiments said penetration-resisting bearing surface continuously surrounds said distal flange surface.

In some embodiments said abutment comprises a plurality of angularly spaced apart surface portions having a cumulative area forming said penetration-resisting bearing surface.

In some embodiments said combination further comprises said distal portion of said tool having a lumen dimensioned to be intimately and slidingly engaged by said rod while limiting bending of said rod to a bend radius of greater than 0.35 meter.

In some embodiments said combination further comprises said distal portion of said tool having a lumen dimensioned to be intimately and slidingly engaged by said rod, wherein said lumen has an internal diameter of between about 100.5 percent and about 300 percent of an outside diameter of said rod.

In some embodiments said combination further comprises a rod tracking tube having an axial lumen dimensioned to be intimately and slidingly engaged by said rod wherein a difference between an outside diameter of said rod diameter and an inside diameter of said lumen diameter is less than about 2.0 mm.

In some embodiments said rod is axially retractable with respect to said abutment.

In some embodiments said combination further comprises a uni-directionally activated rod withdrawing mechanism housed in a cavity within said member; wherein said withdrawing mechanism is configured to manually cause proximal axial movement of said rod.

In some embodiments said withdrawing mechanism comprises: a movable beam within said cavity; a pushbutton acting upon said beam; and, said rod having a proximal extremity secured to said beam.

In some embodiments said movable beam comprises an axially translatable portion.

In some embodiments said movable beam comprises a radially deflectable portion.

In some embodiments said abutment comprises: a distally open-ended cup structure axially aligned with said distal segment; and, wherein said cup has an internal geometry diametrically commensurate with a proximal cap of said plug; whereby said penetration-resisting bearing surface is located axially distal to said radial prominence.

In some embodiments said combination further comprises: said cup comprising a radial prominence supporting said bearing surface; and, at least one radial notch angularly adjacent to said support structure.

In some embodiments there is provided a tool for inserting a punctal plug into the opening of a meatus, said tool comprises: a hand-graspable member; a rod extending distally from said member; said rod having a distal segment elongated along an axis, said distal segment having a free distal rod end; and, an abutment located an axial distance proximal from said distal rod end; wherein said abutment comprises: a radial prominence supporting an penetration-resisting bearing surface a radial distance from said distal segment; wherein said penetration-resisting bearing surface is shaped, dimensioned, and located to directly or indirectly bear against at least part of the tissue surrounding said opening during insertion of said plug into said meatus.

In some embodiments said penetration-resisting bearing surface is shaped and dimensioned to prevent over-penetration of said distal segment into said meatus.

In some embodiments said combination further comprises: a detachable punctal plug which comprises: a body elongated along a first elongation axis, said body having a distal insertable portion, and a proximal cap having a distal flange surface; wherein said plug has an axial bore; and wherein said distal segment is shaped and dimensioned to be fully and removably insertable into said bore.

In some embodiments said penetration-resisting bearing surface extends at least 0.1 mm beyond a maximum radial extent of the shank of the plug being inserted.

In some embodiments there is provided a method for seating a plug in the punctum of a patient, wherein said plug has a proximal cap having a distal flange surface for resting against the tissue surrounding the opening of said punctum, said method comprises: selecting an oblong inserter tool including a rod having a distal segment having a free distal rod end, and an abutment located an axial distance proximal from said distal rod end, said abutment supporting a penetration-resisting bearing surface having a radial dimension greater than a maximum radial dimension of said shank; releasably carrying a punctal plug on said distal rod end; pushing said plug axially through said punctum until said penetration-resisting bearing surface prevents further axial movement of said tool; releasing said plug from said tool; and, axially pulling said tool away from said plug.

In some embodiments the penetration-resisting bearing surface directly contacts a portion of the tissue surrounding said opening thereby preventing over-insertion of the rod and plug into the punctum and canaliculus.

In some embodiments the penetration-resisting bearing surface indirectly contacts, through said cap, a portion of the tissue surrounding said opening thereby preventing over-insertion of the rod and plug into the punctum and canaliculus.

In some embodiments said selecting further comprises: choosing an inserter tool so that said penetration-resisting bearing surface has a radial dimension which is at least 0.1 mm larger than the maximum radial dimension of the shank.

In some embodiments said method further comprises: preventing bending of said rod to a bend radius of less than 0.35 meter during said pushing.

In some embodiments said method further comprises: preventing bending of the rod; preventing inadvertent early retraction of the rod from the plug; and, preventing the plug from bending or falling off during insertion.

In some embodiments said method further comprises: viewing a portion of said tissue surrounding said opening through a gap in said penetration-resisting bearing surface.

In some embodiments said releasing comprises axially retracting said rod from an axial bore in said plug.

In some embodiments said method further comprises prior to said pushing, inserting a pre-sized dilator located on said tool into said punctum, wherein said dilator is dimensioned according to one of a plural number of sizes for said plug.

In some embodiments said releasably carrying comprises: holding said plug where said distal flange surface is located in a first position an axial distance apart from said penetration-resisting bearing surface.

In some embodiments there is provided that in a surgical tool for inserting a plug into the punctal opening of a meatus, wherein said plug comprises a body elongated along a first elongation axis, said body having a distal insertable portion, and a proximal cap having a distal flange surface oriented to rest against tissue surrounding said opening when properly inserted, and an axial bore, wherein said tool comprises a rod having a distal segment removeably insertable into said bore, an improvement which comprises: said distal segment terminating in a distal rod end; an abutment located an axial distance from said distal rod end; wherein said abutment comprises: a radial prominence supporting an penetration-resisting bearing surface oriented to bear against tissue surrounding said opening during insertion of said plug into said meatus.

In some embodiments there is provided a tool for inserting a punctal plug into the opening of a meatus, said tool comprises: a hand-graspable member; a rod secured to said member; said rod having a distal segment elongated along an axis, said distal segment having a free distal rod end; and, an abutment secured to said distal segment an axial distance from said distal rod end; wherein said abutment comprises: a radial prominence supporting an penetration-resisting bearing surface a radial distance from said distal segment; wherein said penetration-resisting bearing surface is located to bear directly or indirectly against at least part of the tissue surrounding said opening during insertion of said plug into said meatus.

In some embodiments there is provided a tool which overcomes the above-described shortcomings by providing an improved ophthalmic instrument for dilating a punctum and safely and accurately inserting a plug, in which the cross-diameter of the meatus-dilating shaft is calibrated to the desired size. In some embodiments there is provided a tool having a cup having an internal geometry commensurate with the external shape and size of the cap is axially mounted at the end of the plug inserting shaft for securely holding and directing the plug during the insertion procedure.

In some embodiments there is provided that in a surgical tool for inserting a plug into the punctal opening of a meatus having a given diameter, wherein said plug comprises a body elongated along a first elongation axis, said body having a distal insertable portion, and a proximal cap having a distal flange surface oriented to rest against tissue surrounding said opening when properly inserted, an improvement which comprises: a median member having a proximal portion, a distal portion, and an elongated tip projecting from said distal portion; a holder for releasably securing said plug to said tip; and, an penetration-resisting bearing surface located at an axial position coplanar with or distal to said flange surface when said plug is properly positioned within said meatus.

In some embodiments said holder comprises: a radial prominence supporting said bearing surface axially spaced distally apart from said tip; and, at least one radial notch angularly adjacent to said radial prominence.

In some embodiments said at least one radial notch extends axially a first axial length.

In some embodiments said at least one radial notch extends angularly a first angle.

In some embodiments said at least one radial notch extends distally to an extent to form an angular discontinuity in said bearing surface.

In some embodiments said at least one radial notch has an outer opening larger than an inner opening.

In some embodiments said at least one radial notch is shaped and dimensioned to have a first angular dimension at a first axial location and a second angular dimension at a second axial location.

In some embodiments the tool further comprises a pane of translucent material covering a portion of said notch.

In some embodiments said portion includes an entire angular and axial dimension of said notch.

In some embodiments said elongated tip projects along said first elongation axis along which the plug is ejected from the cup.

In some embodiments said cup has an insertion axis.

In some embodiments said insertion axis is oriented at an acute angle to said first elongation axis during insertion of said plug into said meatus.

In some embodiments said acute angle is between 0 and 45 degrees.

In some embodiments said holder comprises: a cup terminating said tip and being axially aligned with said tip; and wherein said cup has an internal geometry diametrically commensurate with said cap.

In some embodiments said cup is made from a resiliently flexible, translucent material.

In some embodiments said cup is removably securable to said tip.

In some embodiments said cap is spaced an axial distance apart from said cup.

In some embodiments said axial distance is eliminated when said plug is placed under a given axial mechanical load.

In some embodiments said insertable portion has a largest cross-diameter slightly larger than said given diameter; wherein said plug has an axial bore; and wherein said tool further comprises a rod running axially within said tip and cup and having a distal extremity removably insertable into said bore.

In some embodiments said tool further comprises a unidirectionally activated withdrawing mechanism housed in a cavity within said member; wherein said withdrawing mechanism is configured to manually cause withdrawal of said distal extremity from said cup.

In some embodiments said cap is spaced an axial distance apart from said cup; and wherein said axial distance is eliminated when said withdrawing mechanism activated.

In some embodiments said withdrawing mechanism comprises: a movable beam within said cavity; a pushbutton acting upon said beam; and said rod having a proximal extremity secured to said beam.

In some embodiments said movable beam comprises a radially deflectable portion.

In some embodiments said movable beam comprises an axially translatable portion.

In some embodiments said beam is resiliently deflectable and said rod is resiliently deformable.

In some embodiments said rod is permanently deformable.

In some embodiments said tool further comprises a radial slot extending axially along said median member, wherein said slot is shaped and dimensioned to allow for said rod to form a radial bow within said slot when said rod is placed under a given axial mechanical compression load.

In some embodiments a distal extremity of said rod retracts axially under a given axial mechanical compression load.

In some embodiments there is provided a method for seating a plug in the punctum of a patient, wherein said plug has a proximal cap having a flange surface for resting against the tissue surrounding said punctum, said method comprises: selecting an oblong inserter tool having a first end releasably carrying a punctal plug thereon, and a penetration-preventing bearing surface; pushing said tool axially until a contact is made between said bearing surface and a portion of tissue surrounding said punctum; detecting an increase in resistance to further axial pushing while said contact is maintained; stopping further axial pushing in response to said detecting; releasing said plug from said tool; and, axially pulling said tool away from said plug.

In some embodiments said releasing comprises axially retracting a deformable rod from an axial bore in said plug.

In some embodiments the method further comprises prior to said pushing, inserting a pre-sized dilator located on said tool into said punctum, wherein said dilator is dimensioned according to one of a plural number of sizes for said plug.

In some embodiments the method further comprises: carrying said plug where said flange surface is located in a first position an axial distance apart from said bearing surface; and wherein said pushing comprises: allowing said cap to retract proximally when said plug is placed under a given axial mechanical load, so that said axial distance is eliminated and said flange surface is located substantially coplanar with said bearing surface.

In some embodiments the method further comprises: carrying said plug where said flange surface is located in a first position an axial distance apart from said bearing surface; and wherein said pushing comprises: axially retracting a deformable rod from an axial bore in said plug thereby allowing said cap to retract proximally, so that said axial distance is eliminated and said flange surface is located substantially coplanar with said bearing surface.

In some embodiments there is provided the combination of a punctal plug and a tool for inserting said plug into the punctal opening of a meatus; wherein said plug comprises: a body elongated along a first axis; a distal insertable portion; a proximal cap having a distal flange surface oriented to rest against tissue surrounding said opening when said plug is properly emplaced in said meatus; and, wherein said tool comprises: a median member having a proximal portion, a distal portion, and an elongated tip projecting from said distal portion; a holder for releasably securing said plug to said tip; an penetration-resisting bearing surface located at an axial position to resist penetration of said flange surface through said punctum.

In some embodiments said bearing surface and said flange surface are substantially coplanar.

In some embodiments said holder comprises: a cup terminating said tip and being axially aligned with said tip; and wherein said cup has an internal geometry commensurate with said cap.

In some embodiments said bearing surface continuously surrounds said flange surface.

In some embodiments said cap is retractably secured to said holder between an extended position and a retracted position and wherein axial position is substantially coplanar with said distal flange surface when said cap is in said retracted position.

In some embodiments said combination further comprises: said cup comprising a radial prominence supporting said bearing surface; and, at least one radial notch angularly adjacent to said support structure.

In some embodiments said at least one radial notch extends axially a first axial length.

In some embodiments said at least one radial notch extends angularly a first angle.

In some embodiments said at least one radial notch extends distally to an extent to interrupt an angular gap in said bearing surface.

In some embodiments the tool further comprises a punctum and meatus dilator projecting axially from an end of said member opposite said tip, wherein said dilator is dimensioned according to one of a plural number of sizes for said plug.

In some embodiments said dilator comprises: a cylindrical stem having a cross-diameter substantially equal to the cross-diameter of said insertable portion; and a conical spike terminating said stem.

In some embodiments there is provided that in a surgical tool for inserting a plug into the opening punctum of a meatus, an improvement which comprises a cylindrical stem having a cross-diameter commensurate with said plug and a conical spike terminating said stem.

In some embodiments there is provided that in a surgical tool for inserting a plug into the opening punctum of a meatus, wherein said plug includes a cap at a proximal end having a distal flange surface oriented to rest against tissue surrounding said opening, an improvement which comprises: a holder for releasably securing said plug to said tool; and, an penetration-resisting bearing surface located at an axial position commensurate with or distal to said flange surface when said plug is properly positioned within said meatus.

In some embodiments the cap of said plug has a central, axial bore in a proximal face of said cap, and said tool further includes an axial rod extending through said holder and being sized to intimately penetrate said bore, and wherein said improvement further comprises said rod having an extremity translatable in and out of said holder.

In some embodiments said holder comprises a distally open-ended cup structure made from a resiliently flexible, translucent material.

In some embodiments said cap is spaced an axial distance apart from said cup structure.

The content of the original claims is incorporated herein by reference as summarizing features in one or more exemplary embodiments.

BRIEF DESCRIPTION OF THE DRAWINGS

FIG. 6 is a diagrammatic partial cross-sectional side view of an exemplary embodiment of the rod retraction mechanism shown in the plug-holding position.

FIG. 7 is a diagrammatic partial cross-sectional top view of tool of FIG. 6.

FIG. 8 is a diagrammatic partial cross-sectional side view of the tool of FIG. 6 shown in the plug-releasing position.

FIG. 9 is a cross-sectional view taken along line 9-9 of FIG. 6.

FIG. 31 is a diagrammatic partial cross-sectional side view of the tool of FIG. 29 shown in the plug-holding position.

FIG. 32 is a cross-sectional view taken along line 32-32 of FIG. 29.

FIG. 33 is a diagrammatic partial cross-sectional top view of the tool of FIG. 29 showing the rod engaging the deflectable beam.

FIG. 34 is a cross-sectional view taken along line 34-34 of FIG. 29.

FIG. 35 is a diagrammatic partial cross-sectional side view of the tool of FIG. 29 shown in the plug-releasing position.

DESCRIPTION OF THE EXEMPLARY EMBODIMENTS

Figure 2:
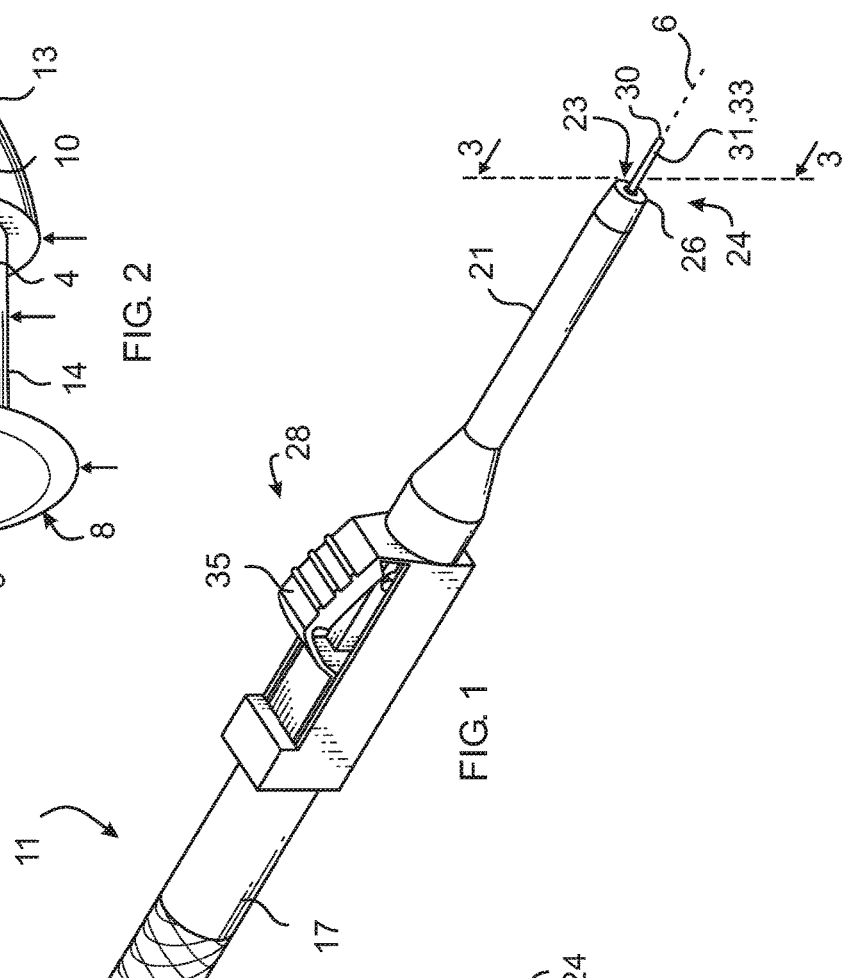
FIG. 2 is a perspective view of a plug.

Referring now to the drawing, there is shown in FIGS. 1-9 a surgical tool 11 according to an exemplary embodiment of the invention and specifically adapted to emplace a spile or plug 12, about 1.4 millimeters in axial length, through the punctal opening of a lacrimal canaliculus meatus 3. In this specification the units "millimeter" or "millimeters" can be abbreviated "mm".

In this exemplary embodiment, as shown in FIG. 2, the punctal plug 12 comprises a body 4 made of a unitary piece of sterile, resiliently deformable, flexible, biocompatible material such as silicone, having a durometer of less than about 80 A, and more preferably less than about 60 A on the Shore durometer scale. The body is elongated along an elongation axis 5. The body has a distal bulb or glanduliform, in the form of a barbed head 13. The head has a largest cross-diameter D2 slightly larger than the internal cross-diameter of the host meatus in order to be frictionally retained in position therein. Thus, it can be forcefully inserted through the punctum and held securely in a canaliculus or other type of meatus. The head is backed by a narrow cylindrical shank 14 having a largest cross-diameter D3 sized to fit snugly within the meatus. The shank terminates in a substantially disk-shaped, flexible, proximal cap 15 having a largest cross-diameter D1 larger than the cross-diameter D3 of the shank and typically larger than or equal to the cross-diameter D2 of the head. A central, axial bore 16 extends through the plug from a circular opening 9 in the proximal face of the proximal cap, through the shank 14, and terminating at a closed end 10 within the head 13. The bore is slightly shorter in length than the plug.

The size of the plug 12 will vary depending on the diameter of the punctum. For emplacement in the punctum of a typical adult human canaliculus, the plug can have a length of between about 1 mm and about 3 mm, and more typically between about 1.2 mm and about 1.75 mm. The plug's proximal cap 15 can have a diameter of between about 0.65 mm and about 2 mm, and for most applications can be on average between about 0.7 mm and about 1.2 mm.

The bore 16 of a typical plug can be between about 0.015 mm and 1.00 mm in diameter, and most typically about 0.28 mm in diameter.

Figure 5:
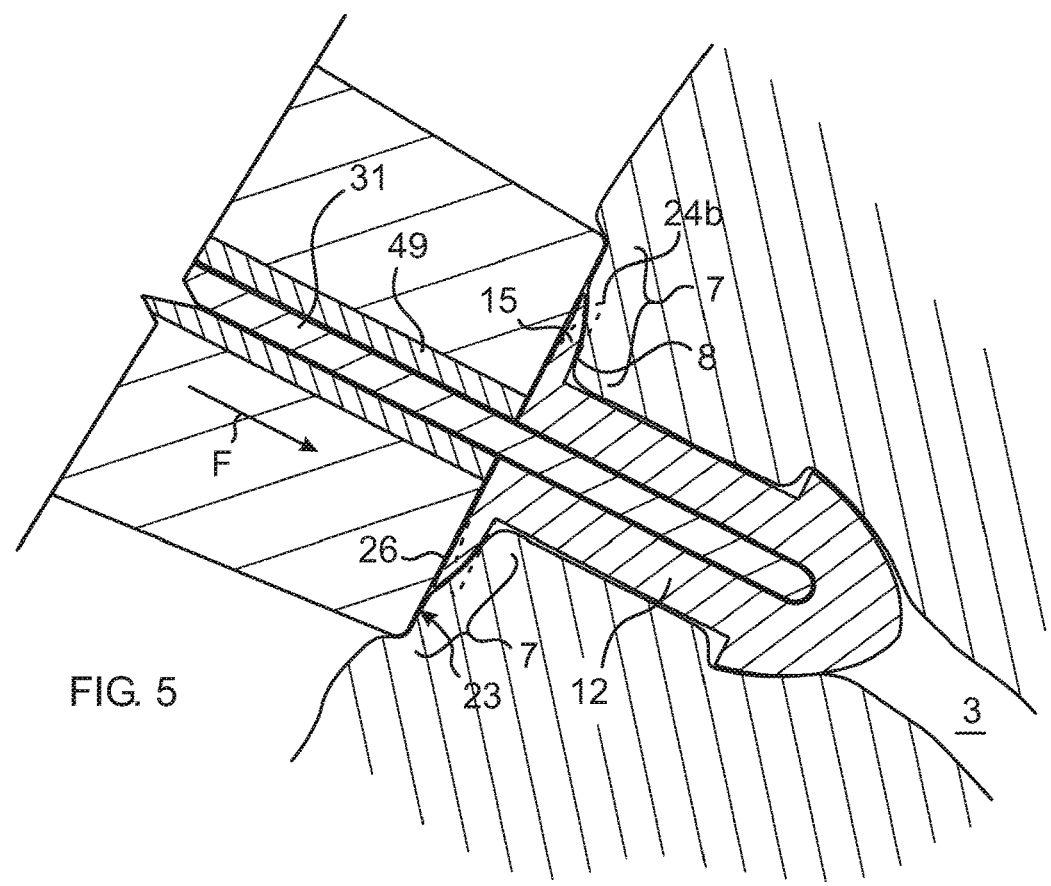
FIG. 5 is a diagrammatic partial cross-sectional side view of the tool of FIG. 1 shown during plug insertion through the punctum.

As shown in FIG. 5, the proximal cap 15 of the plug 12 can terminate in a distal flange surface 8 which is oriented to rest against tissue peripheral to the punctum, in other words a radially inward portion of the zone of tissue 7 surrounding the punctal opening when the plug is properly emplaced in the meatus 3. In this way, the plug can be inserted through the punctal opening of a meatus with the proximal cap remaining on the outside. The plug can eventually be removed from the punctum by grabbing it with tweezers or pincers.

Figure 1:
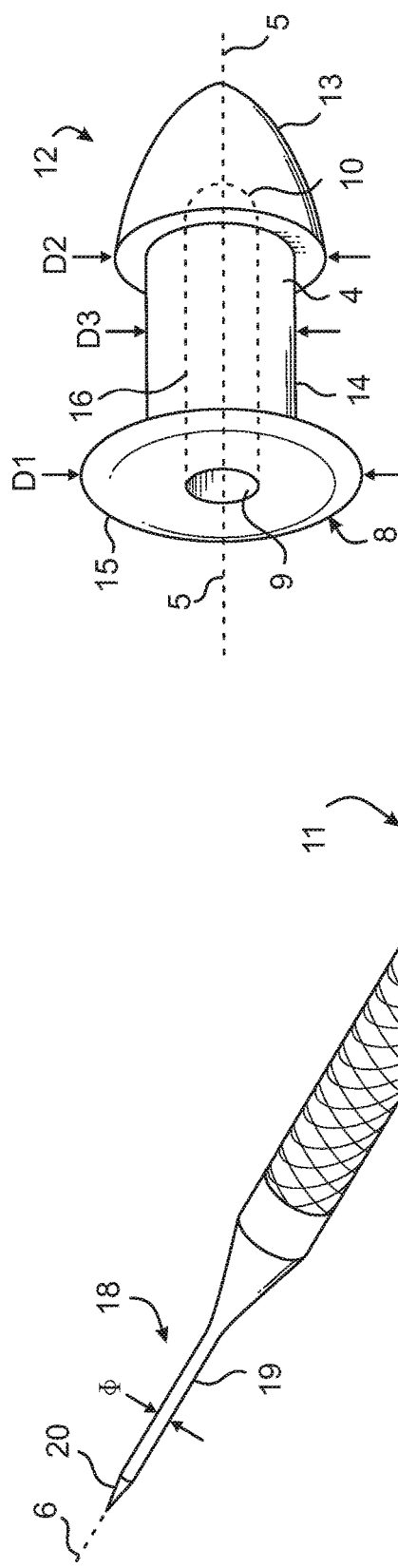
FIG. 1 is a perspective view of a plug-inserting and meatus-dilating tool according to an exemplary embodiment of the invention.
Figure 3:
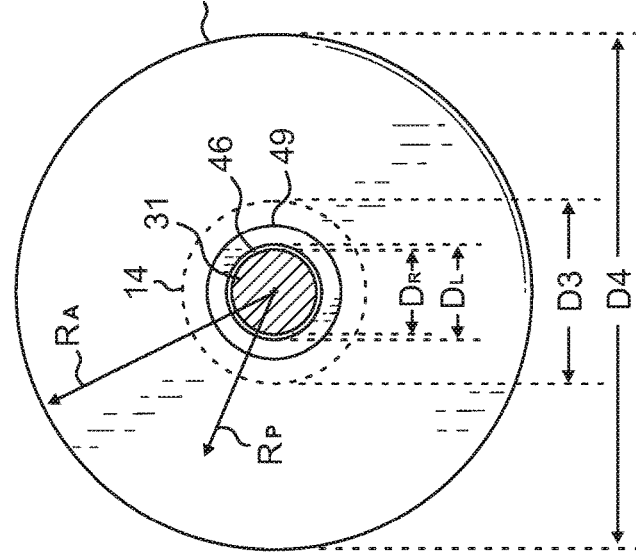
FIG. 3 is a diagrammatic partial cross-sectional end view of the tool of FIG. 1 taken along line 3-3 showing the plug-carrying structure.

Referring now primarily to FIG. 1, the meatus-dilating and plug-inserting tool 11 includes an oblong, generally pencil-shaped member 17 graspable by the hand of a physician. A punctum and meatus-dilating portion 18 is about 20 mm in axial length and consists of a cylindrical stem 19 terminating into a pointed conical spike 20 which projects axially from a first, proximal portion of the member. The spike can be sharp or semi-sharp. The cross-diameter 1 of the stem is selected to reflect the cross-diameter of desired meatus opening. The physician can thus introduce the punctum and meatus-dilating portion 18 through a punctal opening and into a meatus to size it according to the dimensions of the plug. Thus, a differently sized plug can be provided pre-loaded on a tool having an appropriately sized dilating portion for a single use. In other words, the dilator can be dimensioned according to one of a plural number of sizes for the plug. With such a pre-sized dilator, the physician can simply insert the dilator beyond the spike in order to properly dilate the punctum and meatus.

As shown in FIGS. 1-2, a shaft 21, about 30 mm long, projects axially distally from the distal portion of the tool member 17 and is distally terminated by a plug-carrying structure 24 which both securely carries the plug 12 during insertion and provides a penetration-resisting bearing surface 23 which can be sized, shaped, dimensioned, and located to resist and in most cases prevent over-penetration of the plug through the punctum during insertion, and to indicate to the surgeon that the plug has reached its proper penetration position.

The plug-carrying structure 24 can include a thin rod 31 in the form of a semi-rigid, resiliently flexible steel wire which extends distally from the shaft 21 of the tool member 17. The rod can have a distal segment 33 elongated along an axis 6. The distal segment distally terminates at a free distal rod end 30. The distal segment can be shaped and sized to intimately, and fully penetrate the bore 16 in the plug 12 and carry the plug during the insertion process. The outside diameter of the distal segment of the rod can be slightly smaller than the diameter of the bore of the plug in order to help the plug be releasably secured on the distal segment, or can be slightly larger than the diameter of the bore so that the resiliency of the plug better holds the plug in place until the rod is removed. For most punctal plug insertion applications the outside diameter of the distal segment of the rod can be on average about 0.25 mm.

Referring now to FIGS. 1-5, a substantially rigid abutment 26 is located an axially proximal distance Dc from the distal rod end 30. The abutment is essentially a radial prominence extending a radial distance beyond the radial extent of the diameter D3 of the shank 14 of the plug in order to provide the distally facing penetration-resisting bearing surface 23 which limits proximal deformation of the proximal cap 15 during insertion, and, in those situations where the abutment extends radially beyond the diameter of the proximal cap of the plug, contacts and bears against the tissue surrounding the punctum. Thus, the penetration-resisting bearing surface limits axially distal movement of the tool when obstructed by tissue surrounding the punctal opening. In some embodiments the penetration-resisting bearing surface extends at least 0.1 mm beyond a maximum radial extent of the shank, and in some embodiments up to about 5.5 mm beyond the maximum radial extent of the shank. In some embodiments the penetration-resisting bearing surface extends at least 0.1 mm beyond a maximum radial extent of the cap.

The shape and dimension of the abutment 26 can be selected so that the penetration-resisting bearing surface 23 extends a radial distance sufficient to prevent the forceful insertion of the entire plug into the punctum and canaliculus. Therefore, the abutment is sufficiently large to provide enough resistance to further penetration once the cap comes to rest on the tissue surrounding the punctum. This prevents the rod and plug from being pushed too deeply into the punctum and canaliculus. Otherwise, when the abutment is undersized, the abutment and plug will be pushed too deeply into and dilate the punctum and canaliculus. In many applications, the size of the abutment will be larger than the proximal cap of the plug. However, for many large plugs the cap of the plug can radially extend beyond the radial extent of the abutment.

It is important to note again that the abutment 26 functions as a barrier to the axially proximal movement of parts or all of the cap regardless of whether it is smaller, larger, or the same size as the proximal cap 15 because the cap functionally becomes part of the abutment. In other words, the cap of the plug and the abutment together operate as a single penetration-resisting functional unit, avoiding overly deep placement of the punctal plug into the punctum and canaliculus by providing increased resistance to further penetration once the plug is properly seated. In this way the penetration-resisting bearing surface is shaped, dimensioned and oriented to contact either directly or indirectly, by way of the supported proximal cap, the tissue surrounding the punctal opening.

As shown in FIG. 5 the axial position and radial extent of the abutment 26 can be selected to create a penetration-resisting bearing surface 23 which resists over-penetration of the plug 12 into the meatus 3 by contacting, directly and indirectly, through the proximal cap 15 of the plug, some of the tissue in a zone 7 surrounding the punctal opening. In other words, the abutment can be shaped and dimensioned to provide sufficient surface area to prevent forceful placement of the entire plug into the canaliculus, and keep the proximal cap of the plug out of the canaliculus. In addition, part of the abutment can be located to abut the proximal surface of the plug's proximal cap 15 and provide rigid support and thereby limit the proximal deformation of the cap under the force of insertion.

Figure 4:
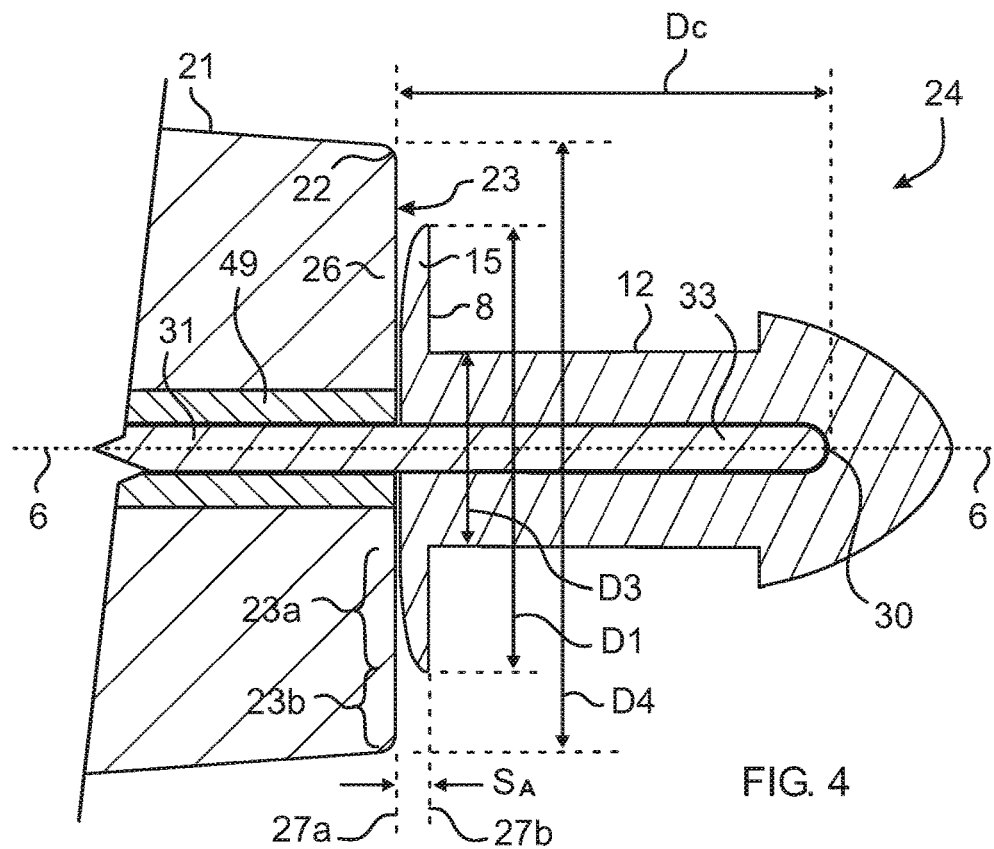
FIG. 4 is a diagrammatic partial cross-sectional side view of the tool of FIG. 1 showing the plug carried by the plug-carrying structure.

As shown primarily in FIGS. 4-5, the abutment 26 can be formed by a simple distal termination of the shaft 21 in a substantially planar, substantially circularly-shaped structure, substantially orthogonal to the axis 6 of the rod. The part of the circularly-shaped structure extending beyond the periphery of the shank 14 of the plug 12 thereby forms the penetration-resisting bearing surface 23, having a diameter D4 which is larger than the diameter D3 of the shank 14. In this embodiment the diameter D4 of the penetration-resisting bearing surface is also larger than the diameter D1 of the proximal cap 15 so that a radially outward portion 23b of the penetration resisting bearing surface extending radially beyond the periphery of the proximal cap can bear directly against part of the tissue 7 surrounding the punctal opening. A radially inward portion 23a bears indirectly against part of the tissue surrounding the punctal opening through the proximal cap which bears directly against the tissue.

During emplacement, the abutment 26 can act as a stiffener to the proximal cap 15 of the plug 12. The radially inward portion 23a of the penetration-resisting bearing surface 23 limits the proximal bending of the resiliently flexible proximal cap 15 from its at-rest position 24 under the pressure of the punctum bearing against it during insertion. In this way the abutment and proximal cap temporarily combine together to form a single functional unit with respect to preventing over-penetration. By rigidly supporting the cap, the abutment causes the distal flange surface 8 of the cap to rigidly bear against part of the tissue surrounding the punctal opening, and not be further deformed and pushed into the punctum. In other words, the penetration-resisting bearing surface 23 can bear against the tissue surrounding the punctal opening directly by way of the radially outward portion 23b, and indirectly by way of the radially inward portion 23a.

The abutment can have a rounded radial periphery 22 to increase comfort during contact with the tissue, and to help avoid damage to that tissue. The abutment can be formed from the same material as the shaft 21, such as rigid plastic. Further, it can be molded simultaneously as the shaft, or formed separately and later bonded to the shaft through gluing, or other means common in the industry.

Care should be taken to avoid dimensioning the abutment to be too large so that it obstructs the physician's view during the plug emplacement procedure.

For plugs being emplaced in the punctum of a typical adult human, the diameter D1 of the proximal cap 15 can often range between about 0.7 mm and 1.2 mm. Thus, for most punctal plug insertion applications the diameter D4 of the penetration-resisting bearing surface can range between about 0.91 mm and about 6 mm. This results in the penetration-resisting bearing surface having a diameter which is between about 75% and about 860% of the radial extent of the plug's proximal cap.

While the plug 12 is properly carried upon the plug-carrying structure 24, the penetration-resisting bearing surface 23 can be said to be substantially axially adjacent to the distal flange surface 8 of the plug. The word "substantially" can be used because minor axial separation may exist between the distal flange surface and the bearing surface when the tool is at rest and when subjected to the forces of insertion. Further, as shown in FIG. 4, both the distal flange surface and the penetration-resisting bearing surface can be substantially planar and fall within planes 27a and 27b respectively. The substantially parallel planes can be separated a minor axial spacing $S_A$ while remaining substantially axially adjacent, substantially radially adjacent and substantially coplanar.

As shown in FIG. 5, the penetration-resisting bearing surface 23 can be located at an axial position substantially coplanar or slightly axially proximal to the distal flange surface 8 of the plug 12 when the plug is properly positioned within the meatus so that the distal flange surface rests against part of the zone of tissue 7 surrounding the punctal opening. At this location the bearing surface simultaneously contacts and bears against the zone of tissue, both directly and indirectly, by way of the plug's proximal cap 15, preventing penetration of the proximal cap into the meatus 3. The penetration-resisting bearing surface is oriented to face in substantially the distal direction which is substantially the same direction as the orientation of the distal flange surface. The size and shape of the penetration-resisting bearing surface is selected so that the maximum axial force F applied during emplacement is insufficient to overcome the frictional counter-force caused by the direct and indirect contact between the penetration-resisting bearing surface and the zone of tissue surrounding the punctal opening.

Referring now to FIGS. 6-9, the tool 11 can include a uni-directionally-activated rod-withdrawing mechanism 28. The mechanism is activated by a pushbutton 35 which axially translates the rod 31 exclusively in the proximal direction in order to precisely disengage the plug-carrying structure 5 from the plug and thereby release it in an emplaced position in the meatus.

The uni-directionally-activated rod-withdrawing mechanism 28 can be housed in a cavity 40 in a median part 41 of the tool member 17. The mechanism can include a pushbutton 35 being hingedly connected to the tool member 17 and acting on a translatable beam 42 slidingly secured at a proximal end 43 to the core of the tool member and tied at its other distal end 44 to the proximal extremity 36 of the rod. The proximal extremity of the rod is formed into a hook structure 37 which dips through and engages a hole 45 formed through the beam. The mechanism is activated by the pushbutton 35 which translates the rod 31 from its plug-holding position shown in FIG. 6 to a plug-disengaged, plug-releasing position shown in FIG. 8.

The rod 31 runs from the hook structure to the plug carrying structure 5 within a rod tracking tube 49 fixed to the tool shaft 21. The purpose of the rod tracking tube is to guide the axial movement of the rod when it is being retracted and to prevent bending of the rod due to the significant axial force applied to the rod during emplacement. A rod which bends or buckles under the insertion force can lead to an inadvertent reduction in the distance between the distal end 30 of the rod and the abutment 26, resulting in imprecise control, and even inadvertent dislodgment of the plug off of the distal segment 33 of the rod. As shown most clearly in FIG. 3, the rod tracking tube has an axial lumen 46 dimensioned to be intimately and slidingly engaged by the rod so that the difference between the rod diameter $D_R$ and the lumen diameter $D_L$ is between about 0.1 mm and about 2.0 mm, and more preferably between about 0.1 mm and about 0.5 mm, and typically about 0.15 mm. Thus, for a tool shaft, and thus a lumen having a length of about 37.5 mm, the bend radius of the rod is kept greater than 0.35 meter, more preferably greater than 1.4 meters, and for some applications greater than 7.0 meters. For a typical a rod having an outside diameter of 0.25 mm, a typical lumen diameter can be about 0.4 mm, which for a tool shaft having a length of about 37.5 mm, results in a bend radius of about 4.6 meters. Depending on the length of the lumen and the diameter of the rod, it has been found that the lumen can have an internal diameter of between about 100.5 percent and about 300 percent of an outside diameter of said rod.

The bend radius has been calculated according to the following formula:

$$r = [L^2/2(D_L-D_R)] + (D_L-D_R)$$

where:
r=the bend radius
L=the length of the lumen
$D_L$=the inside diameter of the lumen
$D_R$=the outside diameter of the rod It's important to note that the rod tracking tube lumen extends the entire length of the tool shaft 21, and nearly the entire length of the rod except for the distal segment 33, and the proximal extremity of the rod 36 including its hook structure 37 extending into the tool's median cavity 40, while the plug is being emplaced.

The rod tracking tube 49 can simply be a lumen integrally formed into the tool shaft 21 from the same material as the shaft such as rigid, injection molded plastic. Alternately, the rod tracking tube can be made from a rigid, durable, malleable material such as stainless steel which is bonded to the shaft. The stainless steel rod tracking tube can often be formed with greater precision than the material of the shaft.

In this embodiment the beam 42 can be resiliently axially translatable so that when the button 35 is released, the beam resiliently returns to its un-translated state. In this way, the release of the button can cause the distal rod end 30 to re-engage into the axial bore 16 of the plug 12 and allow the physician to reposition the plug if desired. Alternately, the button can remain depressed after the button is release so that the rod remains permanently withdrawn.

As shown in FIG. 8, when the pushbutton 35 is depressed by a substantially radial force F, the beam 42 translates axially in the proximal direction 47 and pulls the rod 31 out of the emplaced plug 12 in an axially precise and controlled manner. A receptacle 48 at the proximal end of the cavity 40 provides clearance for the rearward movement of the proximal end 43 of the beam.

The plug can thus be conveniently carried upon the distal segment 33 of the rod 31. The physician can then insert the plug up to, but exclusively of the proximal cap into the punctal opening of a meatus. Pressing the pushbutton 35 liberates the plug 12 in an axially controlled manner from the distal segment and allows for the removal of the tool.

Figure 10:
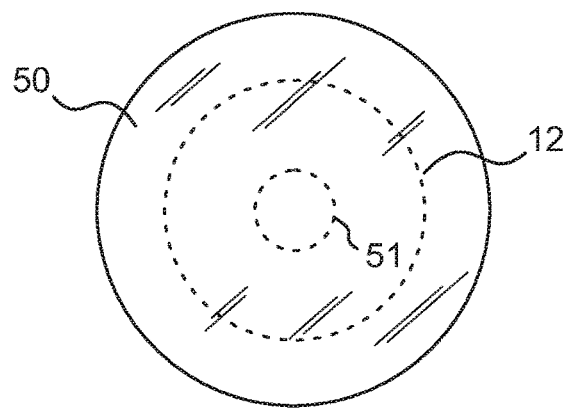
FIG. 10 is a diagrammatic cross-sectional end view of an alternate embodiment of the tool having an abutment made from a pane of translucent material.

In the embodiment of FIG. 1, the circular, disc-shaped abutment 26 completely and continuously surrounds and potentially obscures the view of the plug 12 from near the proximal end of the tool 11. However, as shown in FIG. 10, in order to improve visibility of the plug during insertion, an alternate embodiment of the abutment 50 can be made of rigid, sterile, biocompatible translucent material such as transparent plastic surrounding the rod tracking tube 51 so that the physician can view the plug 12 through the abutment from essentially any angle.

Figure 11:
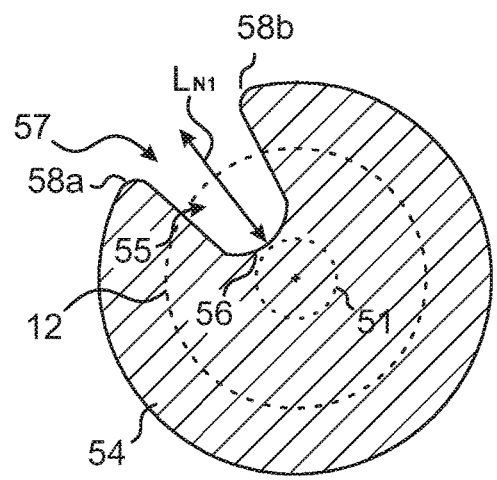
FIG. 11 is a diagrammatic cross-sectional end view of an alternate embodiment of the tool having a viewing notch through the abutment structure.

Alternately, interruptions in the continuity of the penetration-resisting bearing surface can occur without departing from its penetration preventing function. For example, as shown in FIG. 11, an alternate embodiment of the abutment 54 can be adapted to have a radial notch 55 which allows the physician to view a portion of the plug 12 therethrough. The notch extends a radial length $L_{N1}$ from the periphery of the abutment to a radially proximal terminus 56 near the periphery of the rod tracking tube 52. The notch can create an angular discontinuity or gap 57 in the penetration-resisting bearing surface. However, the remainder of the abutment forms a plurality of angularly spaced apart surface portions having a cumulative area forming the penetration-resisting bearing surface. The dimensions of the gap can be maximized to give greater visualization or minimized to provide a greater surface area of the penetration-resisting bearing surface for contacting the tissues surrounding the punctal opening and preventing over-insertion of the plug. In this embodiment the notch is shown having a generally trapezoidal shape having essentially a uniform angular separation. Rounded corners 58a,58b between the notch and the periphery can be provided to avoid sharp edges which may damage tissue and to enhance comfort.

Figure 12:
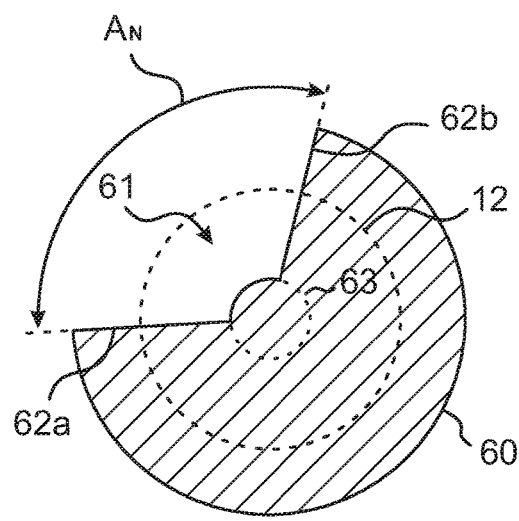
FIG. 12 is a diagrammatic cross-sectional end view of an alternate embodiment of the tool having a wedge-shaped viewing notch through the abutment structure.

As shown in FIG. 12, an alternate embodiment of the abutment 60 can provide a notch 61 in the penetration-resisting bearing surface that has an angular dimension spanning over an angle $A_N$ which can range between about 10 degrees and about 330 degrees. The larger the angle is, the more visibility the notch provides. However, larger angles also result in less bearing surface for contacting the tissues surrounding the punctal opening during insertion. For most applications it has been found that a range of between about 45 degrees and about 180 degrees will be adequate, with an angle within plus or minus 10 degrees of about 150 degrees being found to provide the best balance. In this embodiment, the angular edges 62a,62b of the notch are shown to be substantially linear, creating a substantially wedge-shaped notch. However, the edges can be non-linearly shaped and at various angles to accommodate tradeoffs with greater visibility versus greater contact. The radial length of the notch can extend to the periphery of the rod tracking tube 63 as shown, exposing the plug 12 to view, or be shallower. It shall be noted in this embodiment that the depth of the notch has been selected so that it does not extend into the rod tracking tube.

Figure 13:
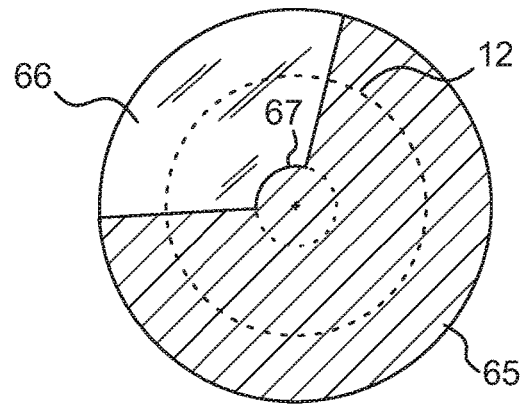
FIG. 13 is a diagrammatic cross-sectional end view of an alternate embodiment of the tool having a wedge-shaped viewing notch through the abutment structure filled with a pane of translucent material.

As shown in FIG. 13, an alternate embodiment of the abutment 65 can provide that the notch be filled with a pane 66 of translucent material such as a rigid, sterile, biocompatible translucent material such as transparent plastic which can extend radially inwardly up to the rod tracking tube 67. This affords a greater area for the penetration-resisting bearing surface while maintaining visibility of the plug 12.

Figure 14:
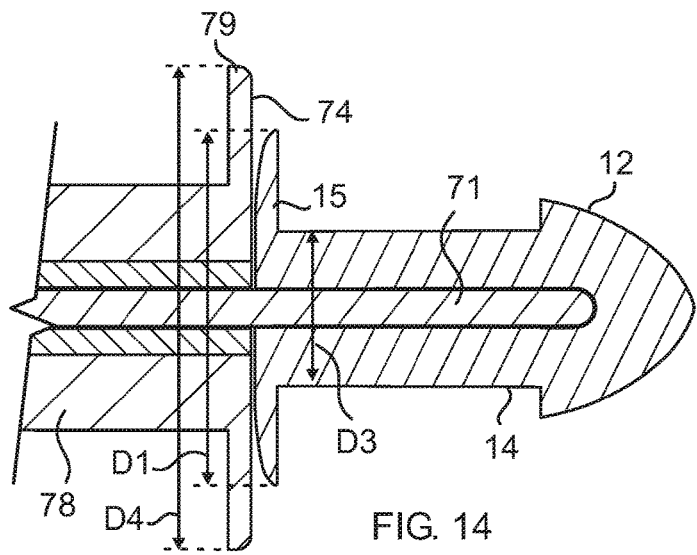
FIG. 14 is a diagrammatic partial cross-sectional side view an alternate embodiment of the tool showing a disk-shaped haft-type abutment at the distal end of the shaft of the tool.

FIG. 14 shows that for those inserter designs using a narrower shaft 78, the abutment can be formed into disk-shaped haft 79 formed onto the distal end of the shaft. It shall be understood that similar to the embodiment of FIGS. 1-5, the haft forms an abutment which provides a radial prominence extending a radial distance beyond the radial extent of the diameter D3 of the shank 14 of the plug 12 in order to provide the distally facing penetration-resisting bearing surface 74 which limits proximal deformation of the proximal cap 15 during insertion and can directly contact part of the tissue surrounding the punctal opening. In this way the diameter D4 of the haft can be selected to be large enough to provide the necessary penetration-resisting bearing surface 74 in order to avoid over-insertion of the plug into the punctum and canaliculus.

Figure 15:
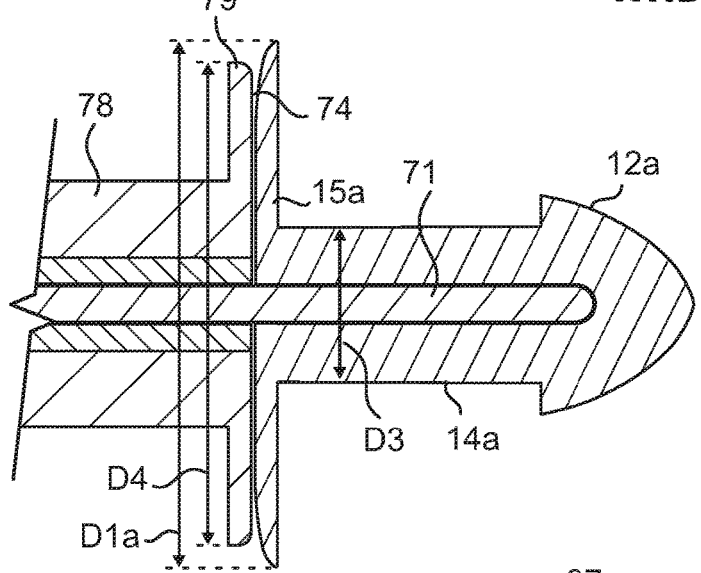
FIG. 15 is a diagrammatic partial cross-sectional side view of the tool of FIG. 14 showing a plug having a proximal cap larger than the abutment.

FIG. 15 shows that for those plugs 12a having a proximal cap 15a having an especially large diameter D1a, the disk-shaped haft 79 located on the distal end of a narrower shaft 78, can continue to provide adequate penetration resistance. Even though the proximal cap diameter D1a is larger than the diameter D4 of the haft 79, the haft continues to provide a radial prominence extending a radial distance beyond the diameter D3 of the shank 14a of the plug in order to provide the distally facing penetration-resisting bearing surface 74 which limits proximal deformation of the proximal cap 15a during insertion. Thus, the diameter D4 of the haft can be selected to be large enough to provide the necessary penetration-resisting bearing surface 74 in order to avoid over-insertion of the plug into the punctum and canaliculus.

Figure 16:
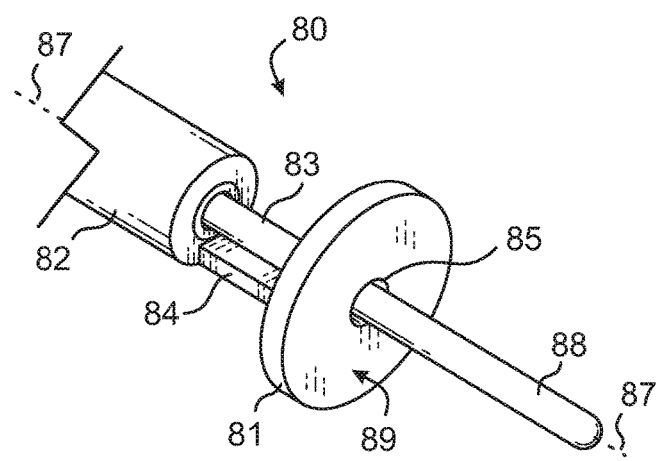
FIG. 16 is a diagrammatic partial perspective view of an alternate embodiment of the tool having a disc-shaped abutment fixed to the shaft of the tool separate from the rod.

FIG. 16 shows an alternate embodiment of the tool 80 having a disc-shaped abutment 81 fixed to the shaft 82 which can provide a penetration-resisting bearing surface 89. A rod 83 having a distal segment 88 extends along an axis 87. The abutment is rigidly supported to the distal end of the shaft by a rigid arm 84 connecting the abutment to the shaft. The rod loosely penetrates through a hole 85 in the center of the abutment in order to carry a plug on its distal rod end 86. The rod can thus retract with respect to the abutment causing the abutment to force the plug from the distal rod end during emplacement.

Figure 17:
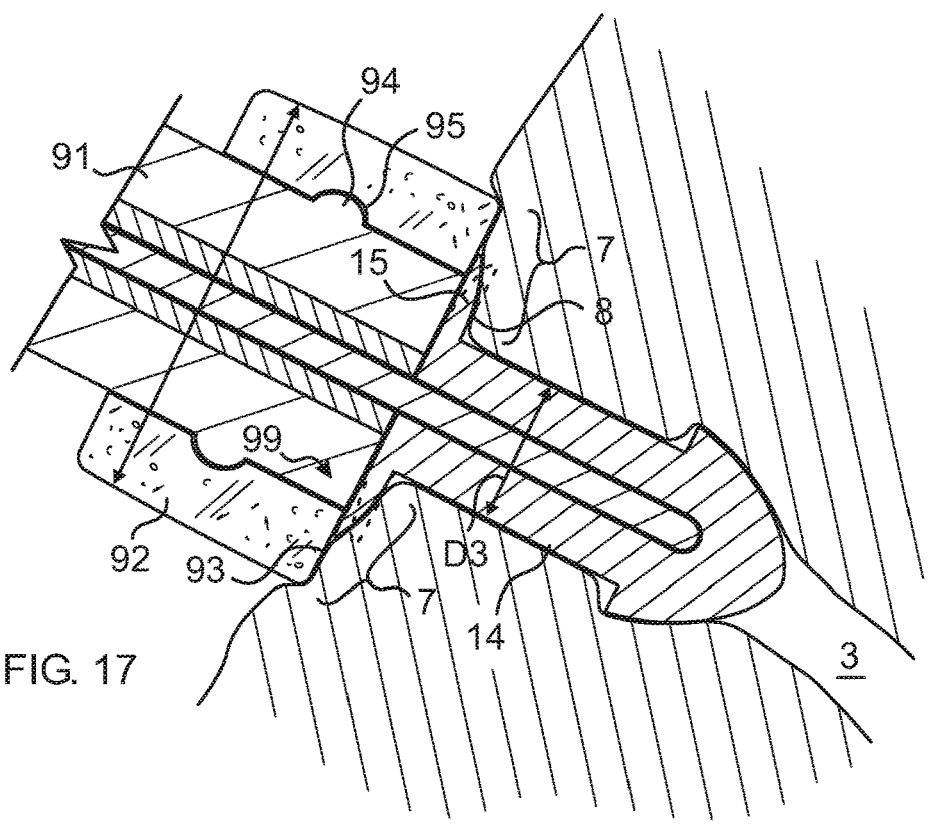
FIG. 17 is a diagrammatic partial cross-sectional side view an alternate embodiment of the tool having a resiliently deformable band attached to the distal end of the tool shaft during plug insertion through the punctum.

In FIG. 17 there is shown an alternate embodiment of the tool having an abutment 99 formed by a band 92 of resiliently deformable material such as silicone, polyurethane, Teflon brand material, ethylene, or propylene that is mounted to the distal end of the shaft 91 of the insertion tool. The shaft and band form a radial prominence extending a radial distance beyond the radial extent of the diameter D3 of the shank 14 of the plug having distally facing surfaces forming a penetration-resisting bearing surface 83 which limits proximal deformation of the plug's proximal cap 15 during insertion, and, in those situations where the surface extends radially beyond the diameter of the proximal cap of the plug, contacts the tissue surrounding the punctal opening. The mounting of the band to the shaft can be made more robust by a circumferential bead 94 engaging a corresponding circumferential groove 95 in the band. Optionally, a layer of adhesive can be used between some of the surfaces of the shaft contacting the band to more securely bond the band to the shaft. A band having a substantially circular cross-section can be dimensioned to provide an abutment having a diameter D4 large enough to provide the necessary penetration-resisting bearing surface 93 in order to avoid over-insertion of the plug into the punctum and canaliculus.

In this embodiment the distal facing surface of the band is coplanar with the distal facing end surface of the shaft. In other embodiments the two surfaces can be substantially coplanar to accommodate minor variations in manufacturing. Those skilled in the art will recognize that in yet other embodiments, the two surface can be located in different locations with respect to one another depending on the shape of the penetration-resisting bearing surface sought.

The band 92, being made from a resiliently deformable material, allows for enhanced comfort during placement of the plug through the patient's punctum. In addition, the band material can be sterile, biocompatible, and translucent. The band being made from a translucent material allows the physician to better view the plug and punctum during emplacement.

Figure 18:
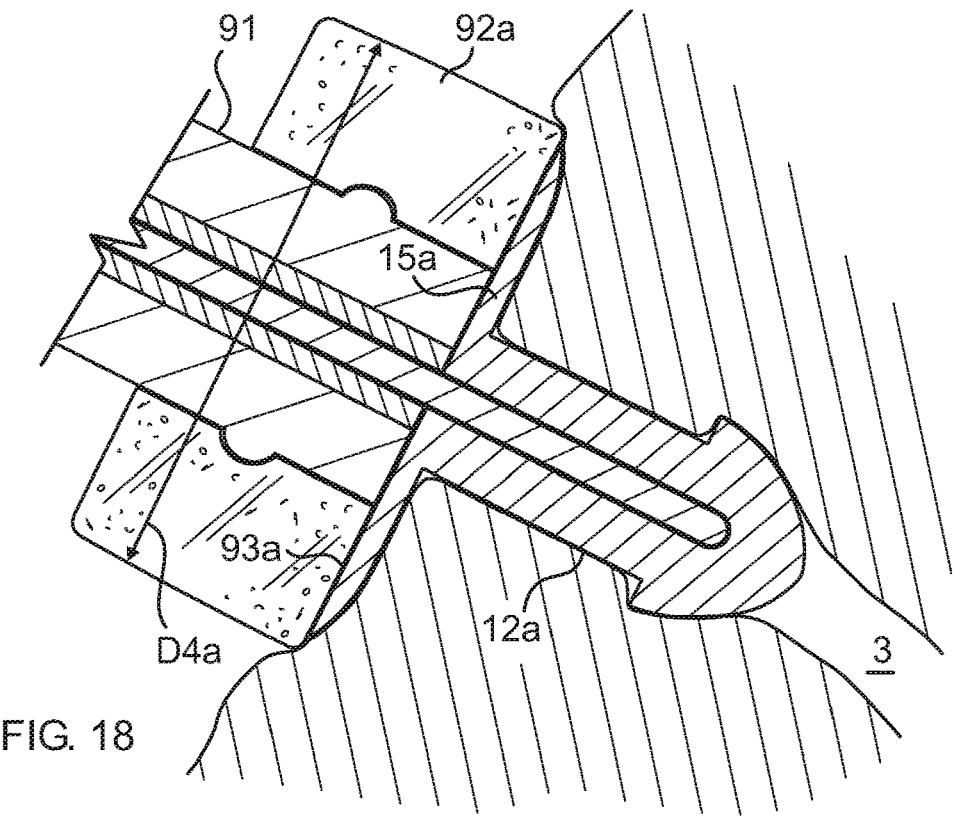
FIG. 18 is a diagrammatic partial cross-sectional side view an alternate embodiment of the tool having a resiliently deformable band having a larger diameter attached to the distal end of the tool shaft during plug insertion through the punctum.

As shown in FIG. 18, by using a detachable and replaceable band the size and shape of the abutment can be adjusted to suit the needs of varying plug insertion parameters. For example, using the same tool shaft 91 from the embodiment of FIG. 17, the radial extent of the penetration-resisting surface 93a can be adjusted by adding or replacing a band 92a having a larger diameter D4a in order to better accommodate a plug 12a having a larger diameter proximal cap 15a.

Figure 19:
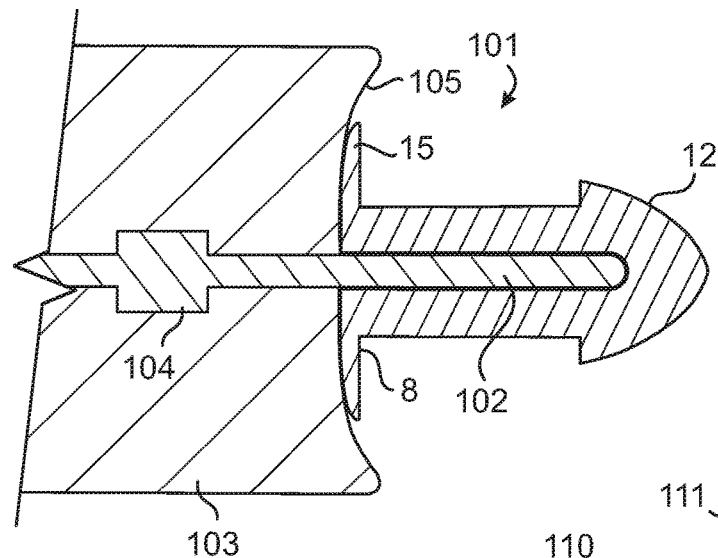
FIG. 19 is a diagrammatic partial cross-sectional side view an alternate embodiment of the tool showing an axially fixed rod and a concave, scalloped, dish-shaped abutment formed on the end of the tool shaft.

FIG. 19 shows an alternate exemplary embodiment of the plug-carrying structure 101 where the rod 102 is fixedly attached to the shaft 103 of the tool by an axial movement-prohibiting cuff 104 connected to the rod and imbedded within the shaft. The distal end of the shaft can be shaped and dimensioned to form a substantially concave, scalloped, dish-shaped abutment 105 oriented to contact the proximal surface of the proximal cap 15 of the plug 12, and to limit the axial movement of the cap in the proximal direction during insertion, thus creating a temporary penetration-resisting bearing surface on the distal flange surface 8 of the cap. In this embodiment, the diameter of the abutment is selected to provide a sufficient penetration-resisting bearing surface to prevent inadvertent insertion of the entire plug into the punctum and canaliculus. The concave dish shape can increase friction so that a smaller diameter abutment may provide the same penetration resistance force as a larger diameter, planar, disk-shaped abutment.

Figure 20:
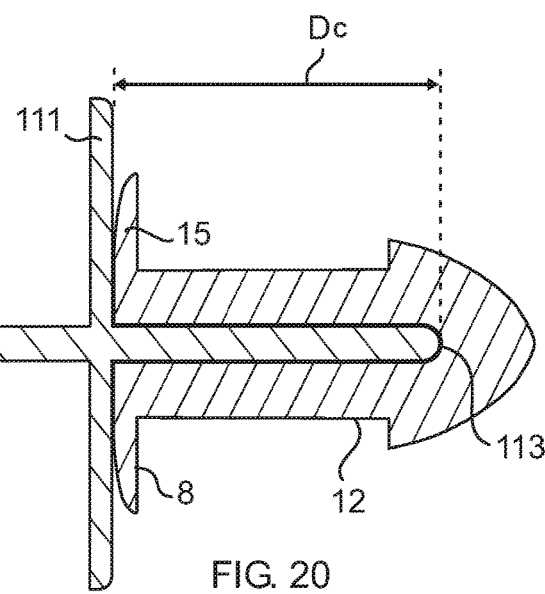
FIG. 20 is a diagrammatic partial cross-sectional side view an alternate embodiment of the tool showing a disk-shaped abutment fixedly attached to the rod.

FIG. 20 shows an alternate exemplary embodiment of the plug-carrying structure 110 where the abutment 111 can be a disk-shaped structure attached to the rod 112 located a distance Dc from the distal rod end 113. In this embodiment the rod may or may not be retractable. A non-retractable rod can be simpler and less expensive to manufacture. A retractable rod including a fixed abutment attached thereto gives the surgeon the ability to precisely withdraw the rod axially by depressing the button while keeping their hand steady. In such an embodiment care must be taken to ensure the friction between the plug and the rod can be easily overcome by the friction of the plug with the meatus.

Figure 21:
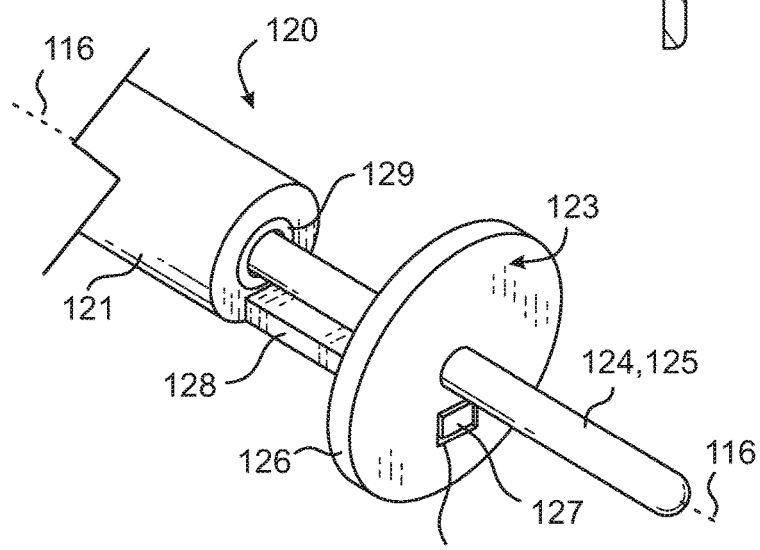
FIG. 21 is a diagrammatic partial perspective view of an alternate embodiment of the tool having a disc-shaped abutment fixed to the rod and an ejection arm extending from the shaft through a window in the abutment.

FIG. 21 shows an alternate embodiment of the tool 120 having a disc-shaped abutment 126 fixed to the shaft 121 which can provide a penetration-resisting bearing surface 123. A rod 124 having a distal segment 125 extends along an axis 116 can retract axially within a rod support tube 129 fixed to the shaft and having a central lumen sized to provide sliding contact with the rod. The abutment is rigidly connected to the rod. Further, in this embodiment, the shaft of the tool fully angularly enwraps the rod support tube. A radially offset rigid ejection arm 128 extends axially from the distal end of the shaft to penetrate through an axial window 122 through the abutment. The arm terminates distally in a distal tip 127 having a distal surface substantially coplanar with the distal surface of the abutment. As the rod and abutment are retracted, the tip of the arm contacts the proximal cap of the plug and forcibly ejects it from the rod.

Figure 22:
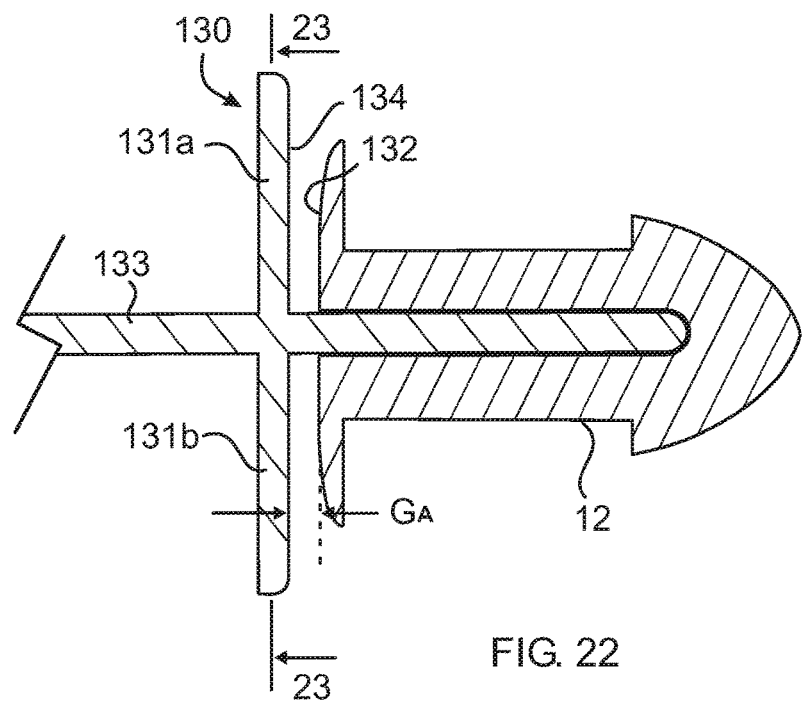
FIG. 22 is a diagrammatic partial cross-sectional side view of an alternate embodiment of the plug-carrying structure having radial paddles providing the penetration resistant bearing surface.
Figure 23:
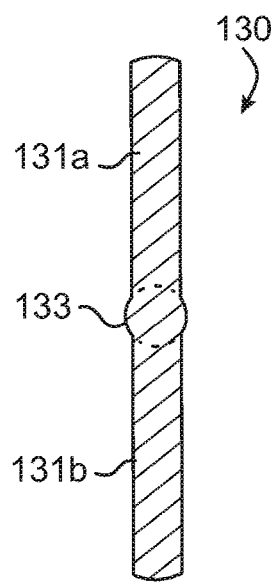
FIG. 23 is a cross-sectional end view taken along line 23-23 of FIG. 22.

As shown in FIGS. 22-23, an alternate embodiment of the abutment 130 can be shaped in the form of a pair of paddles 131a,131b which extend radially from the rod 133. The paddles act as radial prominences in support of the penetration-resisting bearing surface 134 at the radial distal ends of the paddles. The paddles can extend diametrically opposite one another as shown or at other angles. The paddles thereby form a plurality of angularly spaced apart surface portions having a cumulative area forming the penetration-resisting bearing surface. This embodiment also shows that the abutment can be located at an axial position axially proximal to the proximal end 132 of the plug 12 to create an axial gap GA between the penetration-resisting bearing surface and the proximal end of the plug.

Figure 24:
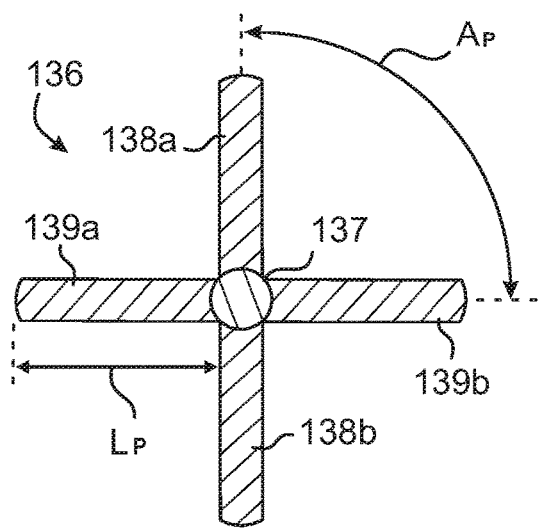
FIG. 24 is a diagrammatic cross-sectional end view of an alternate embodiment of the plug-carrying structure having four angularly evenly spaced radial paddles providing the penetration resistant bearing surface.

As shown in FIG. 24, an alternate embodiment of the plug-carrying structure provides an abutment 136 similar to the embodiment of FIGS. 22-23 including a first pair of paddles 138a,138b which extend radially from the rod 137. A second pair of paddles 139a,139b extend radially from the rod 137 at an angle $A_P$ with respect to the first pair, which in this embodiment is shown to be about 90 degrees. A paddle 139a can extend a radial length $L_P$ from the rod to its radially distal end. The number of paddles, their individual radial lengths, and their angular position are all selectable depending on the needs of the particular tool. However, in many applications it has been found that two or four paddles evenly spaced apart angularly, and having a paddle length of between about 0.45 mm and about 2.5 mm, usually about 0.85 mm being found to provide adequate performance and flexibility for many types of plug insertion scenarios.

Figure 25:
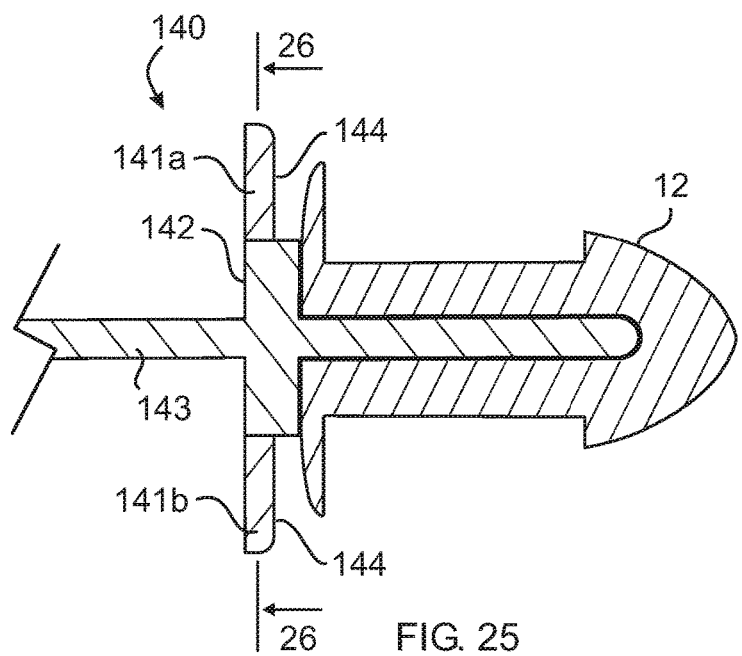
FIG. 25 is a diagrammatic partial cross-sectional side view of an alternate embodiment of the plug-carrying structure having a collar supporting radial paddles providing the penetration resistant bearing surface.
Figure 26:
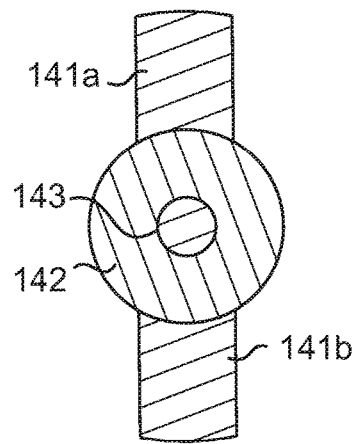
FIG. 26 is a cross-sectional end view taken along line 26-26 of FIG. 25.

As shown in FIGS. 25-26, an alternate embodiment of the abutment 140 can provide a pair of paddles 141a,141b which extend radially from a collar 142 bonded to the rod 143. The paddles act as radial prominences in support of the penetration-resisting bearing surface 144 at the radial distal ends of the paddles. The paddles can extend diametrically opposite one another. The collar provides axial support to the carried plug 12 in situations where axial forces are anticipated which may tend to distort the length of the plug axially in an unwanted manner or risk the distal rod end puncturing the plug bore.

Figure 27:
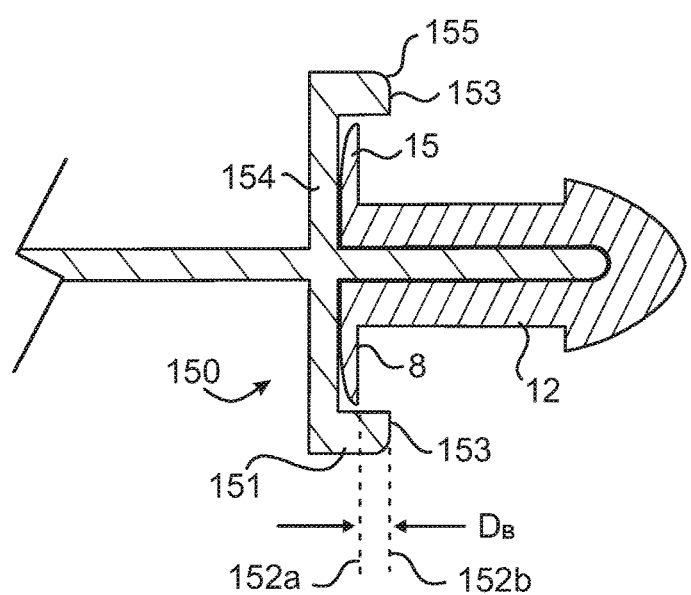
FIG. 27 is a diagrammatic partial cross-sectional side view of an alternate embodiment of the plug-carrying structure having an abutment forming an open-ended cup structure where distal rim provides a penetration resistant bearing surface.

As shown in FIG. 27, an alternate embodiment of the plug-carrying structure provides an abutment 150 including a substantially cylindrical, distally open-ended cup structure 151 having an axially distal rim forming the penetration-resisting bearing surface 153. It is important to note that the penetration-resisting bearing surface can be ring-shaped and lie substantially within a plane 152b which is axially distal to the plane 152a of the distal flange surface 8 of the carried plug 12 separated by an axial distance $D_B$. The cup structure can be formed by merely forming a cylindrical wall extending distally from the periphery of the abutment disk 154. Alternately, the two surfaces can be exactly or essentially coplanar.

In this embodiment, the radially distal lip 155 of the rim of the cup 153 can be rounded to afford additional comfort. In this embodiment, the internal geometry of the cup structure is selected to substantially match the outline of the proximal cap 15 of the plug 12. In other words, the cup can be commensurate with the outline of the proximal cap.

In this way the penetration-resisting bearing surface can be located axially distal to the distal flange surface of the plug during insertion. It shall be noted the cylindrical wall of the cup structure can be axially shortened so that the penetration-resisting bearing surface can be located axially proximal to the distal flange surface of the carried plug. In this way the cup structure provides added stability to the plug while being carried on the tool.

Figure 28:
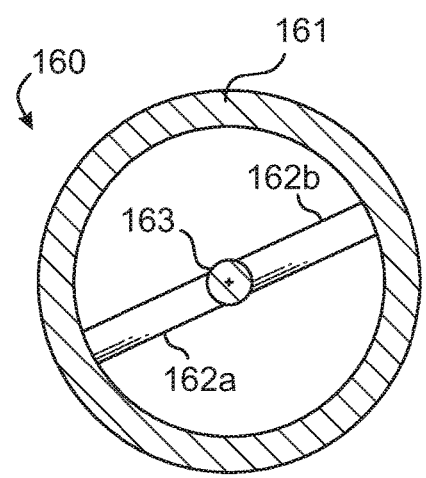
FIG. 28 is a diagrammatic cross-sectional end view of an alternate embodiment of the tool having a ring-shaped structure providing the penetration resistant bearing surface supported by radial prominences extending from the rod.

Referring now to FIG. 28, there is shown an alternate embodiment of the plug-carrying structure in which the abutment 160 includes a distally open-ended cup structure formed by a substantially cylindrical wall structure 161 supported by a pair of radial prominences 162a,162b in the form of spokes extending from the rod 163. The distal rim of the wall provides a continuous, planar, ring-shaped penetration-resisting bearing surface. In this embodiment the axial length of the cup structure can be selected to locate the continuous penetration-resisting bearing surface at essentially any axial location relative to the plug, and still afford good plug visualization between the paddles.

Figure 29:
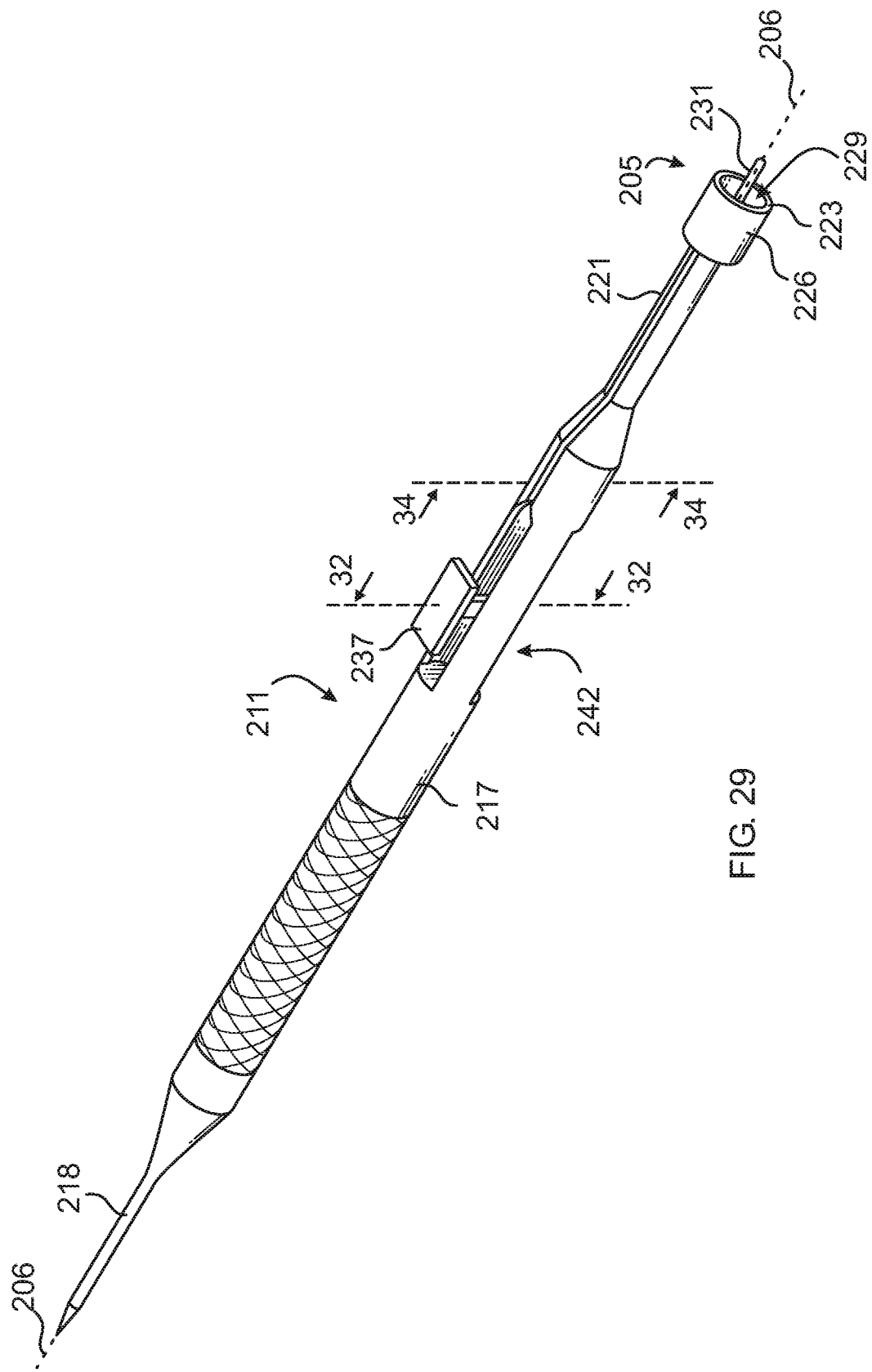
FIG. 29 is a perspective view of a plug-inserting and meatus-dilating tool according to an alternate exemplary embodiment of the invention.

Referring now primarily to FIG. 29, there is shown an alternate exemplary embodiment of a meatus-dilating and plug-inserting tool 211 which includes a pencil-shaped, hand-holdable member 217, elongated along an axis 206, graspable by the hand of a physician. A punctum and meatus-dilating portion 218, similar to the embodiment of FIG. 1, projects axially from a first, proximal portion of the member. A shaft 221, about 30 millimeters long, projects axially from the distal portion of the tool member 217 and is distally terminated by a plug-carrying structure 205 which securely carries a punctal plug 212 on a rod 231 which is axially retractable by depressing a button 237 on a medial part the member 217.

Figure 30:
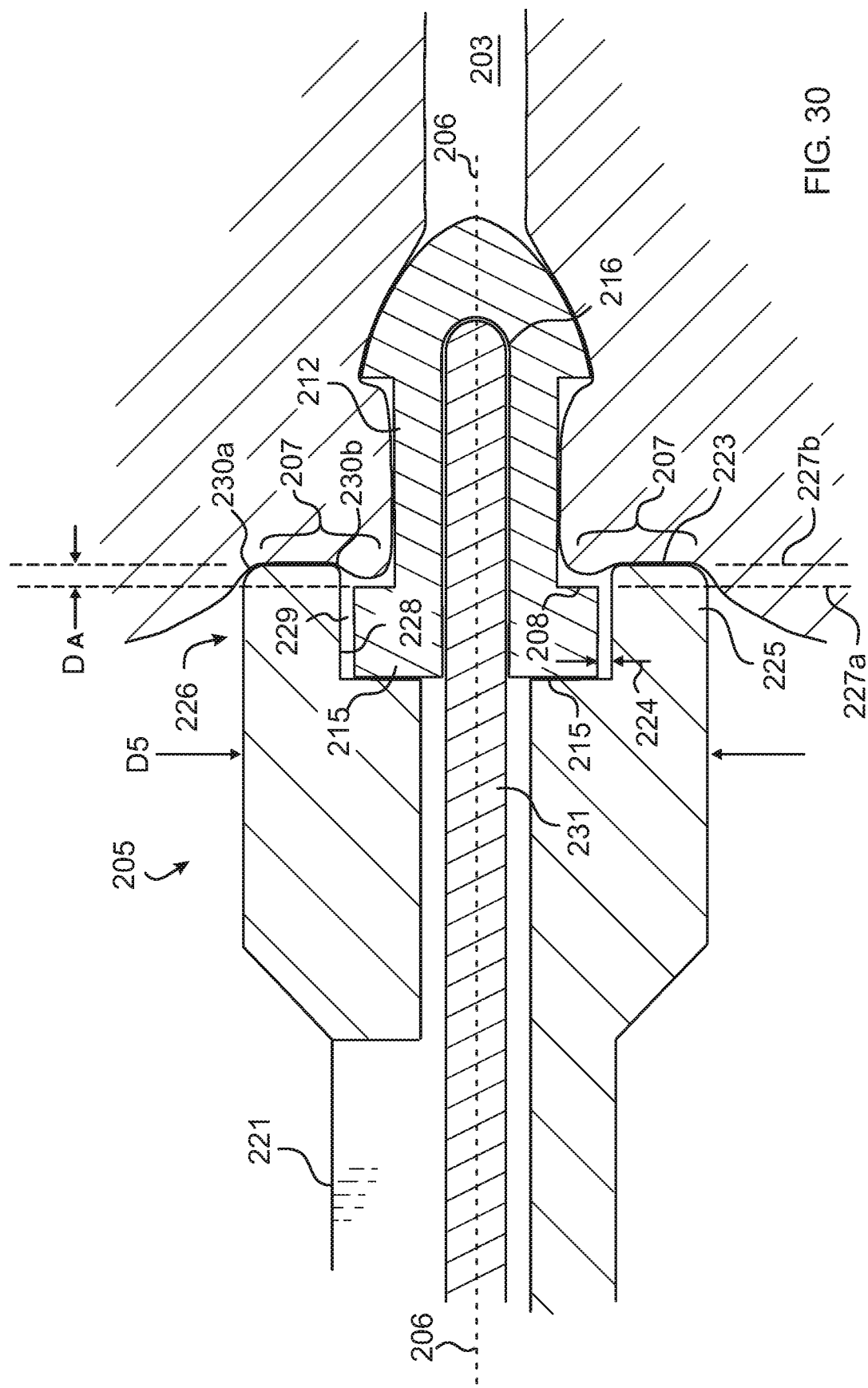
FIG. 30 is a diagrammatic partial cross-sectional side view of the tool of FIG. 29 showing the plug carried by a cup-shaped plug-carrying structure according to an alternate exemplary embodiment of the invention.

Referring now to FIG. 30, during insertion into a meatus 203, the plug-carrying structure 205 provides an penetration-resisting bearing surface 223 sized, shaped, dimensioned, and located to bear against a portion of the tissue 207 surrounding the punctal opening and thereby resist and in most cases prevent over-penetration of the plug 212, and/or to indicate to the surgeon that the plug has reached its proper penetration position. The penetration-resisting bearing surface 223 is supported by a radial prominence 225 formed by a distally located, distally open-ended cup 226 formed onto the distal end of the shaft 221. The substantially cylindrical cup 226 is oriented substantially coaxially with the major axis 206 of the shaft. The cup has a generally axially cylindrical wall 228 terminating a substantially circular distal rim which forms the penetration-resisting bearing surface 223 circumferentially surrounding a substantially circular distal opening to a substantially cylindrical internal cavity 229 and extending radially beyond the radial extent of the proximal cap 215 of the plug 212 thus leaving the small annular gap 224. Thus the cup can have an internal geometry that is substantially diametrically commensurate with the proximal cap of the plug.

In this embodiment, the axial location of the penetration-resisting bearing surface 223 is selected to be slightly distal to the distal flange surface 208 of the plug 212. In other words, the shape of the penetration-resisting bearing surface is selected to be substantially planar and located within a plane 227a substantially perpendicular to the major axis 206 of the cup 226 and separated an axial distance $D_A$ from the substantially planar and substantially parallel distal flange surface 208 located within a plane 227b. Alternately, the two surfaces can be exactly or essentially coplanar, or the penetration-resisting bearing surface can be located within a plane proximal from the distal flange surface of the plug.

The diameter D5 of the cup 226 can be selected to provide adequate surface area to the penetration-resisting bearing surface 223 in order to prevent penetration of the cup through the punctal opening but not be so large as to obscure the view of the plug 212 during insertion. Thus, the diameter can preferably between about 1.01 and 3 times the diameter D2 of the proximal cap 215, and more preferably between about 1.1 and 1.8 times the diameter of the proximal cap. In this way, the forces of the penetration-resisting bearing surface 223 against the tissues surrounding the punctal opening 207 are evenly distributed during plug placement, enhancing axial alignment of the plug 212 with the meatus 203.

In this embodiment, the radially distal lip 230a and the radially proximal lip 230b of the rim of the cup 226 are rounded to afford additional comfort. In this embodiment, the internal geometry of the cup is selected to substantially match the outline of the proximal cap 215 at the proximal end of the plug. In other words, the cup is commensurate with the outline of the proximal cap.

Referring now to FIGS. 31-35, there is shown an alternate embodiment of a punctal plug insertion tool including a thin rod 231 in the form of a resiliently flexible steel wire runs from a plug-carrying cup structure 226 within a slot 234 to a cavity 235 in a median part of the tool member 217. The distal extremity 230 of the rod is sized to intimately penetrate the bore 216, about 0.25 millimeter in diameter, in the plug 212 and, in this embodiment, hold the proximal cap 215 within the cup and the whole plug at the distal end of the shaft 221 during the insertion process.

A uni-directionally activated rod-withdrawing mechanism 245 housed in the cavity 235 and activated by a pushbutton 237 translates the rod 231 from its plug-holding position shown in FIG. 31 to a plug-disengaged, plug-releasing position shown in FIG. 35. The mechanism consists of the pushbutton acting on a deflectable beam 238 fixedly secured at one end 239 to the core of the tool member 217 and tied at its other distal end 232 to the proximal extremity of the rod. The proximal extremity of the rod is formed into an upturned hook structure 240 which dips through a vertical hole 247 formed through the beam. The hole is partially overlapped by a portion of the pushbutton post 248 where it connects to the beam. This creates a crook 246 which is engaged by the proximal tip 244 of the hook structure. This structure provides an easily assembled anchorment between the proximal extremity of the rod and the beam. The beam can have a thinned portion 249 near the end 239 secured to the tool to adjust the force necessary to cause deflection.

In one embodiment the beam 238 can be resiliently deflectable and the rod 231 resiliently deformable so that when the button 237 is released, the beam resiliently returns to its un-deflected state and the rod returns to its un-deformed state. In this way, the release of the button can cause the distal extremity 236 of the rod to re-engage into the axial bore 216 of the plug 212 and allow the physician to reposition the plug if desired. Alternately, the rod can be substantially permanently deformable so that release of the button does not cause the distal extremity to re-extend distally toward the plug. In this way, there is no chance that the distal extremity of the rod will re-engage the bore 216 in the plug.

As shown in FIG. 35, when the pushbutton 237 is depressed, the beam 238 deflects and pulls the rod 231 against the shoulder 241 at the intersection of the slot 234 and cavity 235 causing the rod to slightly translate proximally out of the cup 226 and thus the proximal cap 215 allowing the plug 212 to be released from the cup. A cutout 242 in the wall of the cavity opposite the pushbutton provides clearance for the downward movement of the distal end 232 of the beam.

The plug can thus be conveniently mounted at the distal end of the shaft 221 and have its proximal cap 215 held into the cup 226 by the distal extremity 236 of the rod 231. The physician can then insert the plug up to, but exclusively of the cap into the punctal opening of a meatus. Pressing the pushbutton 237 liberates the plug 212 from the tip and allows for the withdrawal of the tool.

Figure 36:
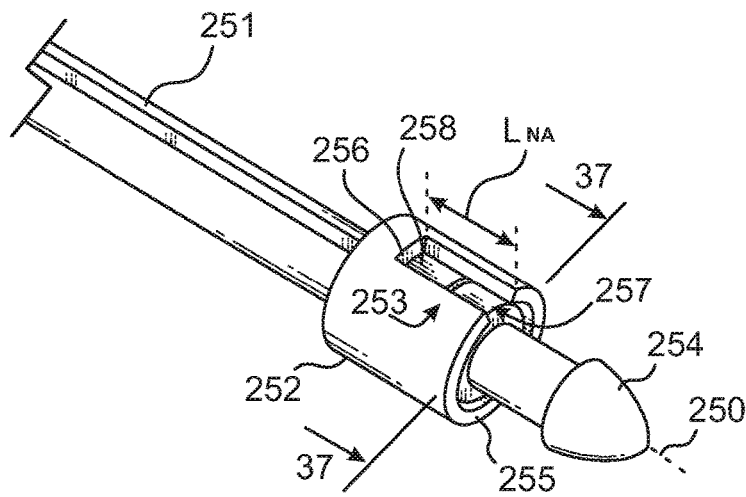
FIG. 36 is a diagrammatic partial perspective view of an alternate embodiment of the tool having a viewing notch through the cup structure.

In the embodiment of FIG. 29, the penetration-resisting bearing surface 223 completely and continuously surrounds the distal flange surface 208 of the plug 212. However, in order to improve visibility of the plug during insertion, interruptions in the continuity of the penetration-resisting bearing surface can occur without departing from its penetration resisting function. For example, in FIGS. 36-37 there is shown an alternate embodiment of an inserter having a distal end of a shaft 251 having a plug-carrying structure formed by substantially cylindrical cup structure 252 having a center axis 250. The cup is adapted to have a notch 253 which allows the physician to view a portion of the plug 254 therethrough. The notch extends an axial length $L_{NA}$ from an axially proximal terminus 256 to an axially distal terminus 257 which, when extended to the penetration-resisting bearing surface 255, also creates an angular discontinuity or gap 257 in the penetration-resisting bearing surface. The dimensions of the gap can be maximized to give greater visualization or minimized to improve the stability of the plug in the inserter and to provide a greater surface area of the bearing surface for contacting the tissues surrounding the punctal opening and preventing over-insertion of the plug. In this embodiment the notch is shown having a generally rectangular shape having essentially a uniform angular dimension along its axial length.

Figure 37:
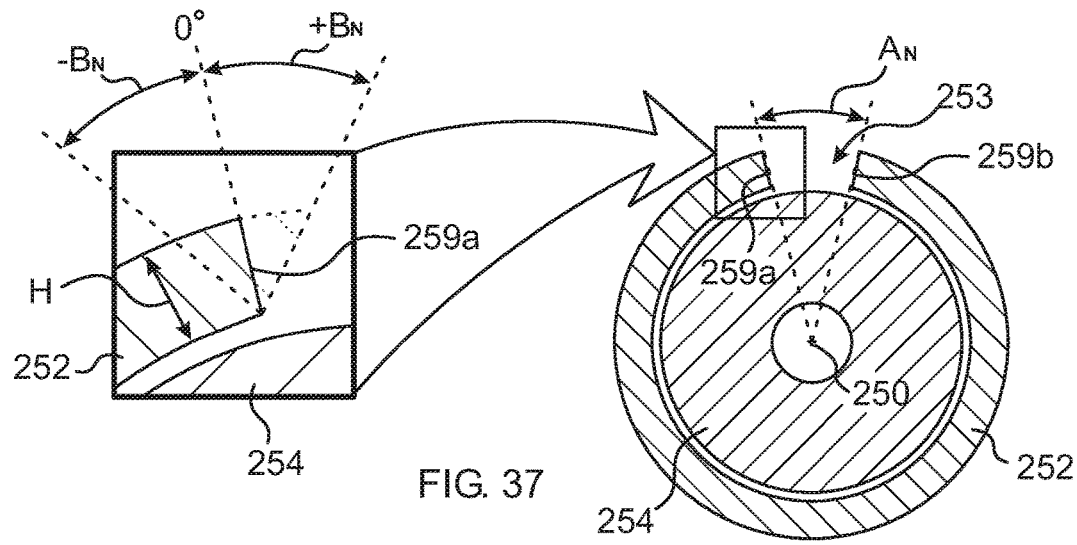
FIG. 37 is a cross-sectional end view taken along line 37-37 of FIG. 36.

As shown in FIG. 37, the notch 253 can have an angular dimension spanning over an angle $A_N$ which can range between about 10 degrees and about 330 degrees. The larger the angle is, the more visibility it provides. However, larger angles also result in less penetration-resisting bearing surface for contacting the tissues surrounding the punctal opening, and potentially less stability provided to the plug during insertion. For most applications it has been found that a range of between about 45 degrees and about 180 degrees will be adequate, with an angle within plus or minus 10 degrees of about 150 degrees being found to provide the best balance. In addition one or more of the angular walls 259a,259b of the notch can be diametrically oriented to the cup. In other words, each of the walls can be located within a plane common to the central axis 250 of the cup 252 as shown thus being at a diametrically 0 degree angle. Alternately, one or more of the walls, or even part of the walls can be oriented at a non-zero angle within a range of angles between $-B_N$ and $+B_N$ with respect to the diametrical orientation. The height H of the walls are selected to provide adequate structural support to the bearing surface of the cup while maintaining a non-bulky outer dimension. For most applications, the height preferably ranges between about 0.1 millimeter and 2.0 millimeters, more preferably between about 0.2 millimeter and 1.2 millimeters in order to balance adequate support with low bulk.

Figure 38:
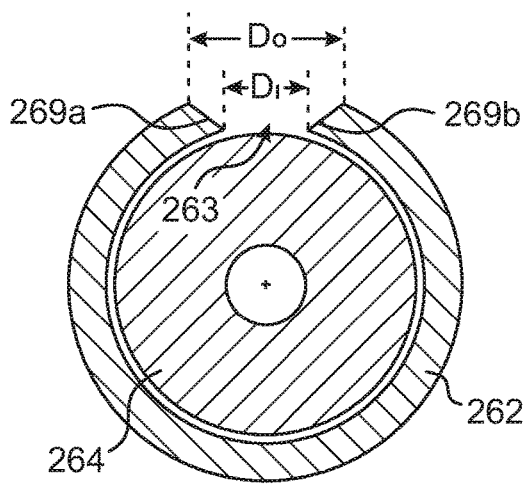
FIG. 38 is a cross-sectional end view showing an alternate notch shape.

Alternately, as shown in FIG. 38, the walls 269a,269b of the notch 263 in the cup 262 can be oriented at an angle that causes the notch to have a wider radially outward opening $D_O$ and a narrower radially inward opening $D_I$. This allows for increased viewing angles, enhancing visibility while maintaining greater contact and thus stability to the plug 264.

Figure 39:
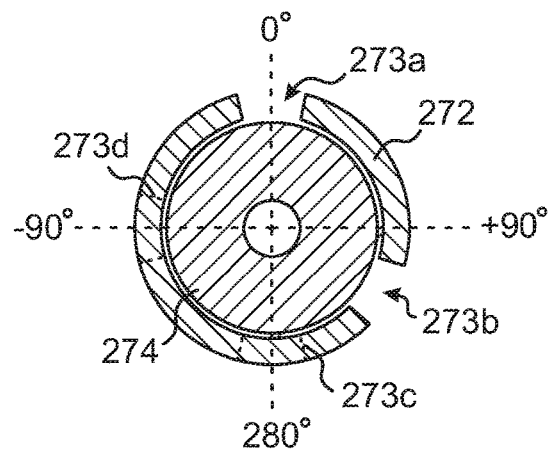
FIG. 39 is a cross-sectional end view showing alternate notch locations.

Alternately, as shown in FIG. 39, one or more notches 273a,273b can be located at various angular positions through the wall of cup structure 272 in order to better visualize the plug 274 during insertion. For example, a first notch 273a can be centered angularly at the 0 degrees or 12 o'clock position. A second notch 273b can be centered angularly at approximately the +120 degrees or the 4 o'clock position. Indeed, the entire circumference of the cup structure is available for locating additional notches 273c,273d for example. Of course, care must be taken to shape, dimension and locate the notches without severely disturbing the functionality of the penetration-resisting bearing surface and plug holding structure. Another advantage is that the one or more notches can be located at other angular locations depending on the preferences of the surgeon and the procedure being conducted.

Figure 40:
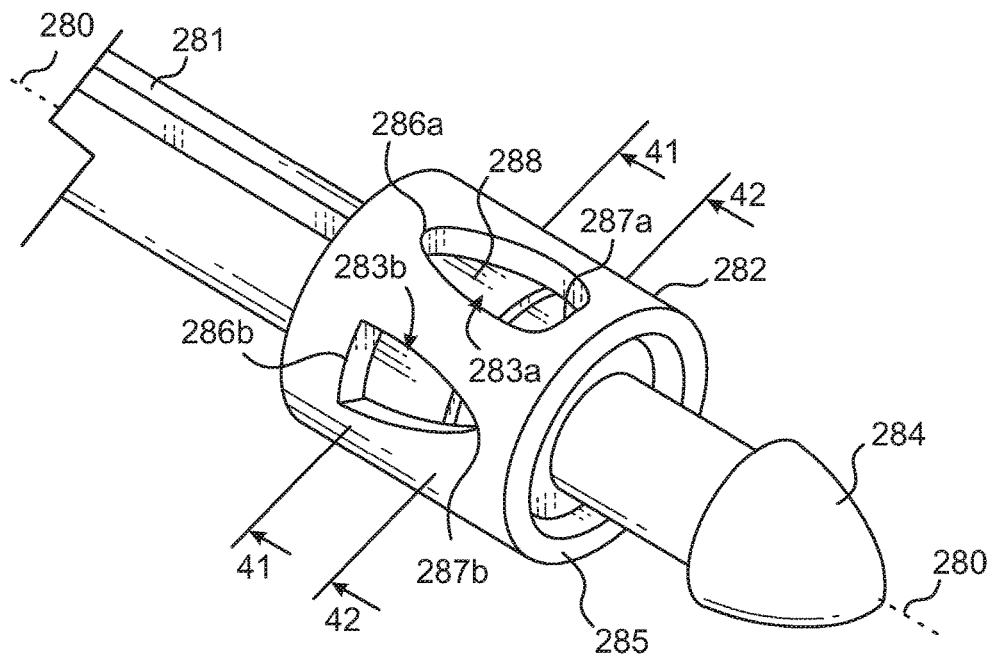
FIG. 40 is a diagrammatic partial perspective view of an alternate embodiment of the tool having a plural number of differently shaped viewing notches through the cup structure.
Figure 41:
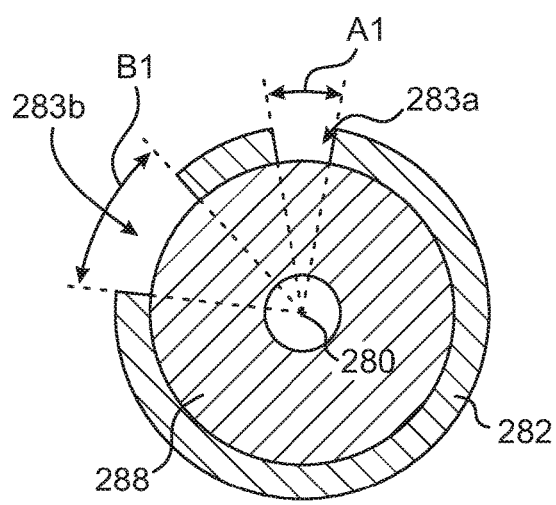
FIG. 41 is a cross-sectional end view taken along line 41-41 of FIG. 40.
Figure 42:
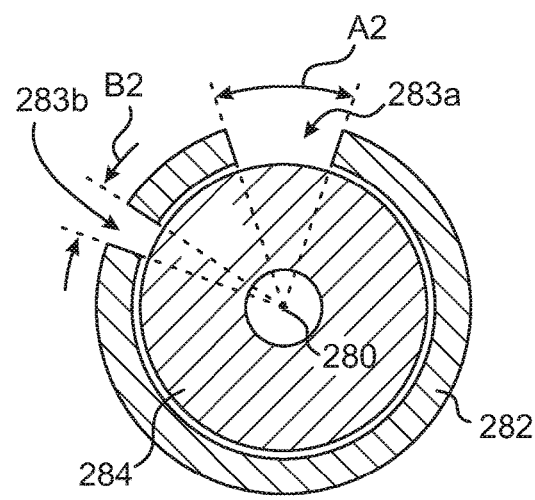
FIG. 42 is a cross-sectional end view taken along line 42-42 of FIG. 40.

FIGS. 40-42 show that the cup structure 282 located at the tip 288 of the shaft 281 elongated along an axis 280 can have one or more notches 283a,283b that are complexly shaped having angular dimensioning which varies according to axial position depending on the desired strength and visibility characteristics. By way of example, the notch 283a is shown having an elongated egg-shape whereas the notch 283b is shown having a generally lanciform shape. The notch 283a can extend axially from a proximal terminus 286a to a distal terminus 287a and have first angular dimension A1 at a first, proximal axial location shown in FIG. 41 and a second angular dimension A2 at a second, distal axial location shown in FIG. 42. Similarly, the notch 283b can extend axially from a proximal terminus 286b to a distal terminus 287b and have first angular dimension B1 at a first, proximal axial location shown in FIG. 41 and a second angular dimension B2 at a second, distal axial location shown in FIG. 42. Thus, it can be understood that a notch 283a can have a narrower angular dimension A1 near the proximal terminus 286a and a wider angular dimension A2 near the distal terminus 287a. By varying the angular dimensioning of a notch according to axial position the tool designed can adjust the strength of the cup structure which affects stability and control of the plug during insertion, and adjust the visibility of the proximal cap portion of the plug 284 against the tip 288 of the shaft 281. This adjustability can be especially useful when a more flexible material is used for the cup structure.

Figure 43:
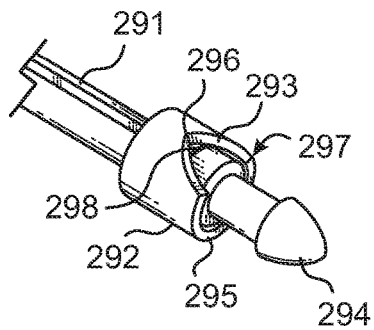
FIG. 43 is a diagrammatic partial perspective view of an alternate embodiment of the tool having a single lanciform shaped notch through the cup structure.

FIG. 43 shows that the cup structure 292 can have a single, complexly shaped notch 293 that extends in a generally lanciform manner from a narrower, rounded or pointed proximal terminus 296 to a widened distal terminus 297 interrupting the penetration-resisting bearing surface 295 to form a gap. The notch has an axial length sufficient to reveal the tip 298 of the shaft 291 in relation to the proximal end of the proximal cap structure of the mounted plug 294.

Figure 44:
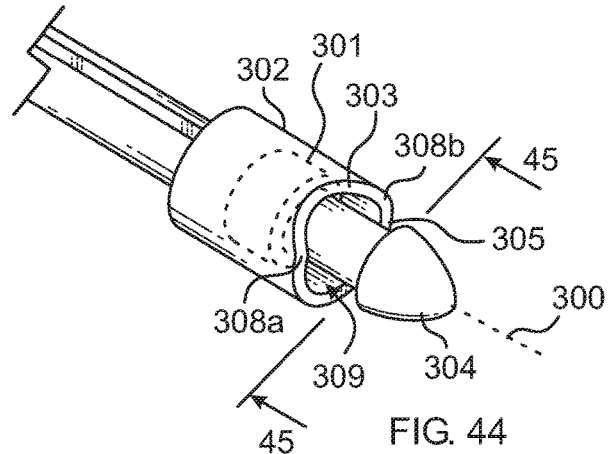
FIG. 44 is a diagrammatic partial perspective view of an alternate embodiment of the tool having a single lanciform shaped notch through the cup structure and a deeper cup internal cavity.
Figure 45:
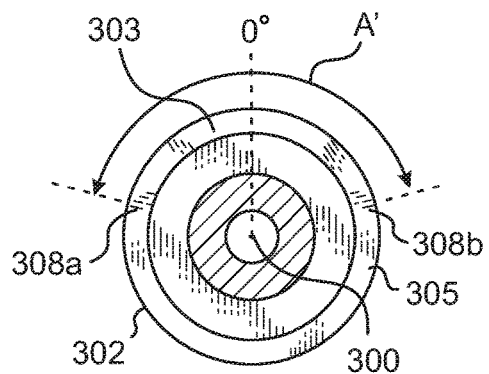
FIG. 45 is a cross-sectional end view taken along line 45-45 of FIG. 44.

FIGS. 44-45 show that the cup structure 302 can have a deeper internal cavity 309 so that the proximal cap 301 of the plug 304 is fully contained within the cavity when the plug is fully seated in the inserter holder prior to insertion. In this embodiment a notch 303 has an axial length which is short enough so that the view of the proximal cap is obscured until the plug starts to be extracted from the cup structure. In this way, the cup structure provides improved stability against forces having a component off the axis 300 of the plug. In addition, the transitions 308a,308b between the notch and the penetration-resisting bearing surface 305 can be rounded to enhance comfort and better avoid minor damage to the tissues contacted. Of course, the use of one or more notches can provide greater visibility of the plug and/or tip prior to and/or during insertion.

Figure 46:
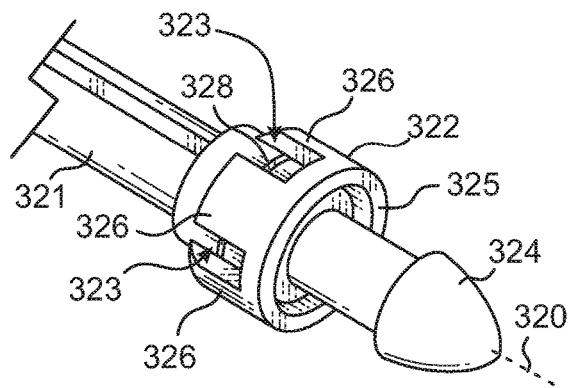
FIG. 46 is a diagrammatic partial perspective view of an alternate embodiment of the tool having a spaced apart prong supported cup structure.

FIG. 46 shows that the cup structure 322 can have a continuous, planar, ring-shaped penetration-resisting bearing surface 325 supported coaxially with the axis 320 of the mounted plug 324 by one or more radial prominences in the form axially and radially extending prongs 326 separated by an equal number of angularly adjacent notches 323. Each prong connects the distal part of the cup structure forming the penetration-resisting bearing surface with the shaft 321 near its distal tip 328. This embodiment maximizes the angular coverage of the bearing surface while providing visualization of the plug's proximal cap in it fully engaged position on the inserter tool.

Figure 47:
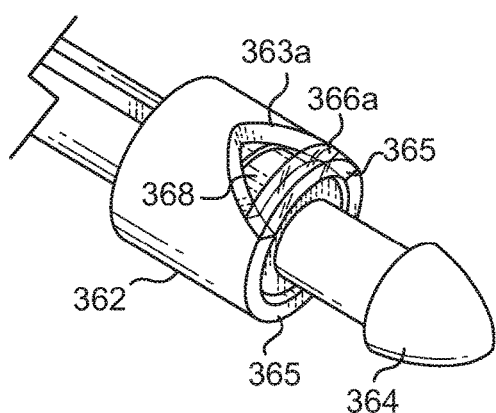
FIG. 47 is a diagrammatic partial perspective view of an alternate embodiment of the tool having a pane of translucent material partially covering a notch through the cup structure.

FIG. 47 shows that the cup structure 362 can have at least one notch 363a that is at least partially covered by a pane 366a of translucent material such as transparent rigid plastic. It further shows that the pane 366a can be shaped, dimensioned and located to cover the most distal portion of the notch 363a so that it provides a continuation of the penetration-resisting bearing surface 365 so that it entirely surrounds the distal opening of the cup through which the plug 364 distally extends. The open proximal portion of the notch not being covered by the pane allows open viewing of the proximal cap 368 of the plug therethrough. By covering a portion of the notch with translucent material, the strength of the cup structure and the stability provided to the plug during insertion can be enhanced while maintaining enhanced visibility. Also, the pane can be used to enhance the penetration-resisting bearing surface provided by the cup lip while maintaining enhanced visibility.

Figure 48:
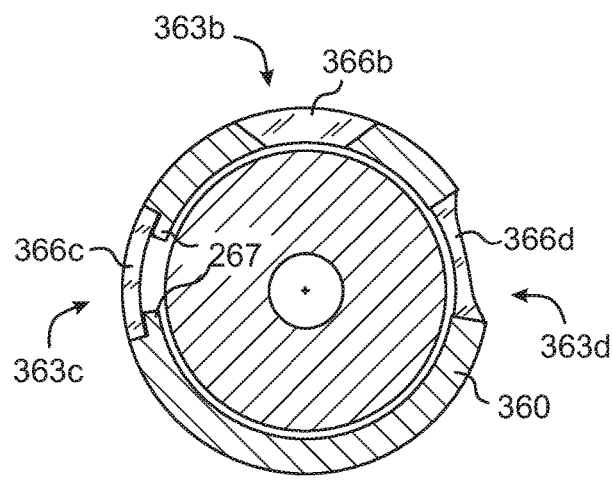
FIG. 48 is a diagrammatic cross-sectional view of an alternate embodiment of the tool having panes of translucent material partially covering a notches through the cup structure.

FIG. 48 shows that for any of the embodiments, the cup structure 360 can have one or more notches 363b,363c,363d that are at least partially or fully covered by a pane 366b, 366c,366d of translucent material such as transparent plastic. For example notch 363b can be shaped and dimensioned similarly to the notch of FIG. 28 and be completely covered by the pane 366b. In other words, the portion of the notch 363b covered by the pane 366b includes the entire angular, axial, and radial dimensions of the notch. Notch 363c shows that the notch walls can have flanges 367 so that a reduced thickness pane 366c can cover the entire angular and axial dimensions of the radially outward portion of the notch. Notch 363d shows that the pane 366d can seal the notch without covering a portion that includes the entire outer angular dimension of the notch by not filling the entire radial dimension of the notch.

Figure 49:
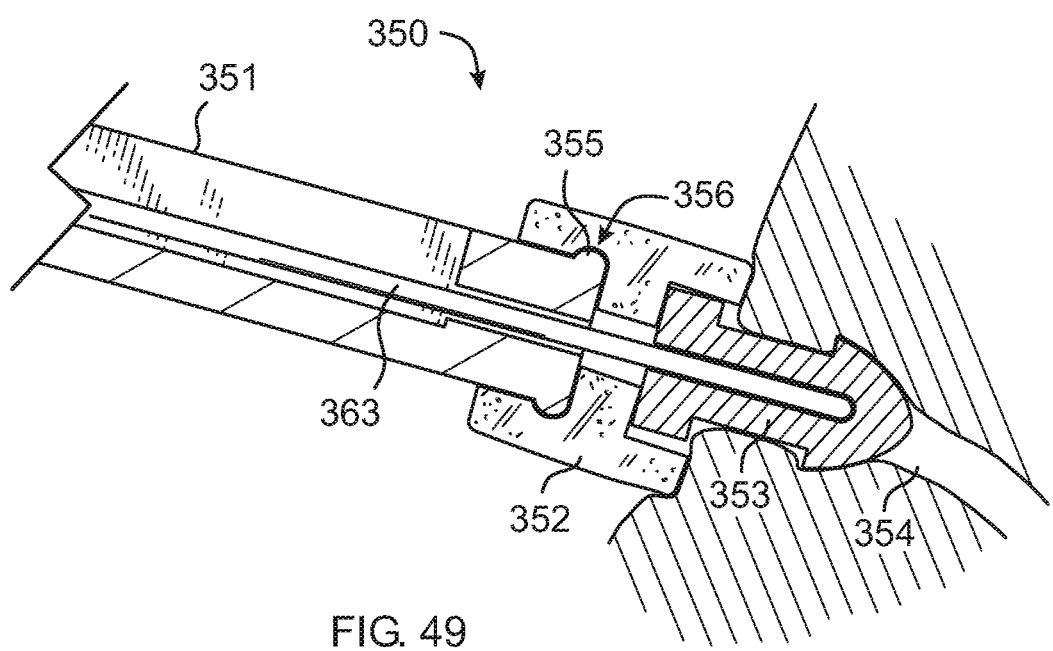
FIG. 49 is a diagrammatic partial cross-sectional side view of an alternate embodiment of the tool having a resiliently deformable plug-carrying structure.

Referring now to FIG. 49, there is shown an alternate embodiment of the tool 350 having a distally projecting shaft 351. A cup 352 made from a resiliently deformable material such as silicone, polyurethane, Teflon brand material, ethylene, or propylene is mounted to the distal end of the shaft. In addition, the cup material can be sterile, biocompatible, and translucent. The mounting of the cup to the shaft can be made more robust by a circumferential bead 355 engaging a corresponding circumferential groove 356 in the cup. The cup material can allow the cup to be removably secured to the distal end of the shaft. Optionally, a layer of adhesive can be used between some of the surfaces of the shaft contacting the cup to more securely bond the cup to the shaft.

The cup 352 being made from a resiliently deformable material allows for enhanced comfort during placement of the plug through the patient's punctum. The cup being made from a translucent material allows the physician to better view the plug and punctum during emplacement.

Figure 50:
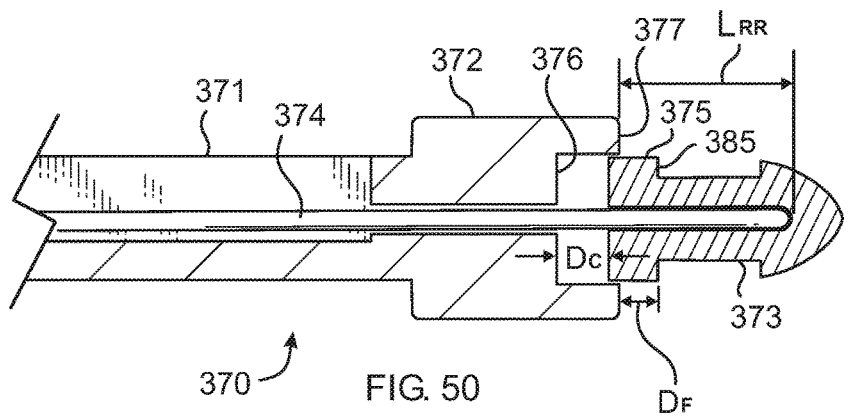
FIG. 50 is a diagrammatic partial cross-sectional side view of an alternate embodiment of the tool having a retractably carried plug in a mechanically unloaded condition.
Figure 51:
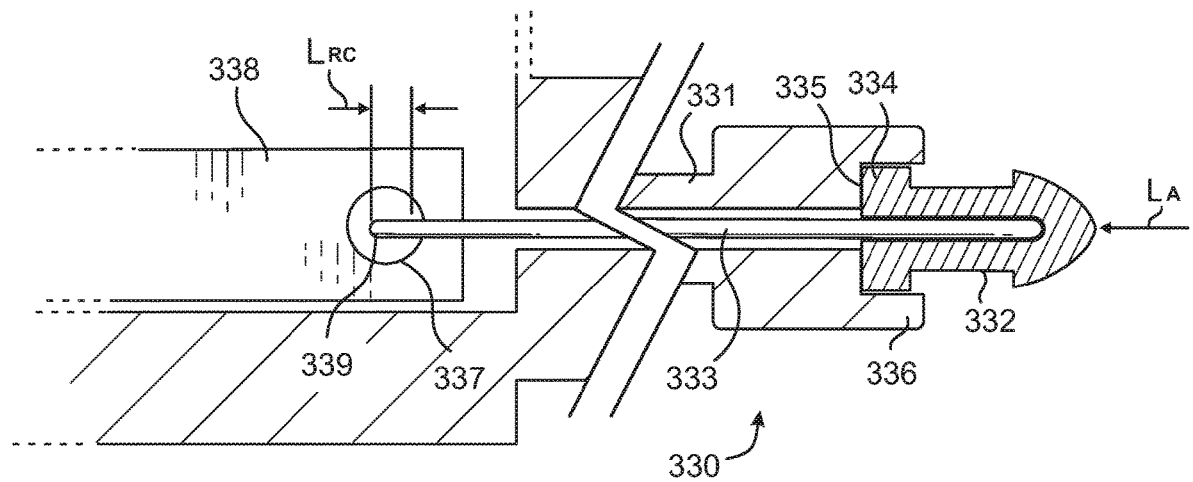
FIG. 51 is a diagrammatic partial cross-sectional side view of the tool having the plug release mechanism of FIG. 6 while under a given axial mechanical load.

Referring now to FIGS. 50-51, there is shown an alternate embodiment of the tool 370 having a distally projecting shaft 371 supporting a coaxially oriented distal cup structure 372 for carrying and orienting a punctal plug 373. In this embodiment the plug is carried distally further out on the tool so that the physician can better see the plug during insertion.

As shown in FIG. 50, when the plug 373 is fully engaged upon the retractable rod 374 and while the plug and rod are at rest under no applied axial mechanical load, the plug is located in a distally extended position where its proximal cap 375 is spaced apart an axial distance $D_C$ from the proximal floor 376 of the cup. Consequently, the distal flange surface 385 of the proximal cap is located a distance $D_F$ from the distal rim 377 of the cup which forms the penetration-resisting bearing surface. In this "at rest" position the rod 374 extends distally beyond the distal rim 377 of the cup by an axial length $L_{RR}$.

Similarly, as shown in FIG. 51, the rod retraction mechanism of the embodiment of FIG. 6 can be can implemented on a tool 330 having the plug-carrying cup structure of FIG. 29 in order to accommodate an axial component load LA which pushes a plug 332 proximally into the cup structure 336 until the proximal cap 334 rests against the tip 335 of the shaft 331 which causes the rod 333 to retract proximally, thus causing the proximal end 339 of the rod to move proximally a distance $L_{RC}$ with respect to hole 337 in the beam 338. Alternately, the physician can activate the push-button (35 in FIG. 6) to retract the rod and allow the plug to seat completely within the cup prior to, or while the plug is being pushed into the meatus. In this way, if the distal end of the plug is bent by non-axial forces or the rod does not retract automatically, the rod will not interfere with proper placement of the plug.

Figure 52:
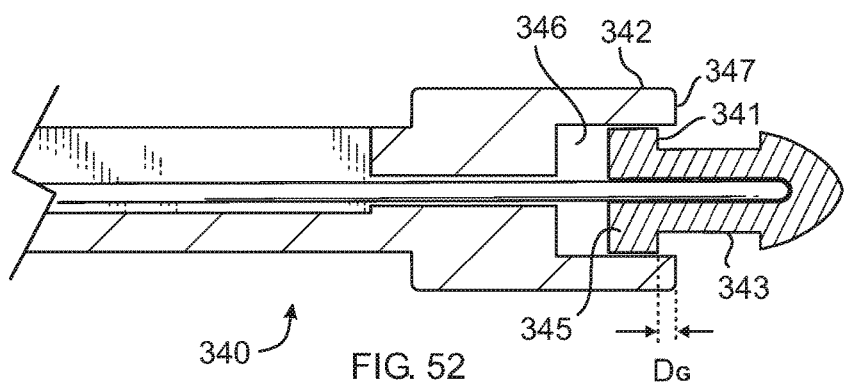
FIG. 52 is a diagrammatic partial cross-sectional side view of an alternate embodiment of the tool having a retractably carried plug in a mechanically unloaded condition with its cap fully recessed within the tool cup.

Referring now to FIG. 52 there is shown an alternate embodiment of the tool 340 similar to the tool of FIG. 50. However, in this embodiment the distal rim forming the penetration-resisting bearing surface 347 of the coaxially oriented distal cup structure 342 is extended, and the internal cavity 346 made deeper so that while the tool is in its "at rest" state without an axial force applied, the punctal plug 343 is carried so that its proximal cap 345 is fully contained in the cup. Thus, the penetration-resisting bearing surface 347 is located a distance $D_G$ axially distal from the distal flange surface 341 of the plug. In this embodiment there is always at least some amount of setback of the flange surface from the bearing surface so that over-insertion is prevented especially in those cases where the meatus is found to be overly dilated or otherwise looser than expected and the plug does not retract as expected when the axial force is applied.

Those skilled in the art of designing punctal plug inserters will readily recognize that some of the various features detailed in the various disclosed embodiments can be utilized in a variety of inserters, including those which use other features. For example, the plug-carrying structures of the embodiments of FIGS. 40, 44, and 46 can use the compressible material of the embodiment of FIG. 49.

The above described tool can be used in the following exemplary embodiment of a method for seating a punctal plug in the punctum of a patient. The plug has a proximal cap having a distal flange surface for resting against the tissue surrounding the punctal opening. The method includes selecting an oblong inserter tool which includes a rod having a distal segment having a free distal rod end, and an abutment located an axial distance proximal from said distal rod end. The distal rod end releasably carries the punctal plug thereon. The abutment supports a penetration-resisting bearing surface having a radial dimension greater than the maximum radial dimension of the shank of the plug. In some embodiments the penetration-resisting bearing surface can have a radial dimension at least 0.1 mm larger than the maximum radial dimension of the shank. In addition, in some embodiments the penetration-resisting bearing surface can be shaped, sized and oriented to bear against the tissue surrounding the punctal opening during insertion. In some embodiments the penetration-resisting bearing surface directly contacts a portion of the tissue surrounding the punctal opening thereby preventing over-insertion of the rod and plug into the punctum and canaliculus. In some embodiments the penetration-resisting bearing surface indirectly contacts a portion of the tissue surrounding said opening thereby preventing over-insertion of the rod and plug into the punctum and canaliculus. This is accomplished by the penetration-resisting bearing surface directly and forcefully contacting the cap of the plug, and limiting the proximal bending of cap during insertion. The supported cap then directly contacts and bears against the tissue surrounding the punctal opening.

The method can also include preventing the bending of the rod to bending radiuses of less than 1.4 meters, and in some embodiments preventing the bending of the rod to bending radiuses of less than 4.6 meters, and in yet other embodiments preventing the bending of the rod to bending radiuses of less than 7.0 meters, by selecting a tool having a lumen through which the rod slides to be small enough to prevent such bending.

With the plug carried on the tool, the tool is grasped and oriented to push the tip of the plug through the punctum. The tool is then pushed axially until the penetration-resisting bearing surface prevents further axial movement of the tool. In some embodiments contact is made between the penetration-resisting bearing surface and a portion of tissue surrounding the punctal opening in order to prevent further axial movement of the tool. The surgeon detects an increase in resistance to further axial pushing while said contact is maintained. Feeling that resistance, the surgeon stops further axial pushing. In some embodiments the surgeon can view a portion of the tissue surrounding the punctal opening through a gap in said penetration-resisting bearing surface, in order to verify that the plug is properly seated in the punctum. The surgeon then releases the plug from the tool by depressing the button of the rod withdrawing mechanism. Once the plug is free of the tool, the surgeon axially pulls the tool away from the punctum and the emplaced plug.

Alternately, the surgeon can predilate the punctum by inserting the pre-sized dilator located on the opposite end of the tool into the punctum.

During emplacement the surgeon can view a portion of the tissue surrounding said punctum through a gap in the penetration-resisting bearing surface of the abutment.

While the exemplary embodiments of the invention have been described, modifications can be made and other embodiments may be devised without departing from the spirit of the invention and the scope of the appended claims.

What is claimed is:

1. The combination of a punctal plug and a tool for inserting said plug into the punctal opening of a meatus;
    wherein said plug comprises:
        a shank having a proximal end and a distal end;
        an insertable portion connected to said distal end; and,
        a proximal cap connected to said proximal end, said cap having a distal flange surface oriented to rest against at least part of the tissue surrounding said opening when said plug is properly emplaced in said meatus;
    wherein said tool comprises:
        a member having a distal portion, and a rod projecting from said distal portion;
        said rod having a distal segment elongated along an axis, said distal segment having a free distal rod end;
        an abutment located an axial distance from said distal rod end;
        wherein said abutment comprises:
            a penetration-resisting bearing surface located at an axial position to resist penetration of said distal flange surface through said punctal opening, thereby preventing over-penetration of said plug into said meatus: and,
            at least one radial notch forming an angular discontinuity in said penetration-resisting bearing surface.

2. The combination of claim 1, wherein said penetration-resisting bearing surface extends beyond a maximum radial extent of said shank.

3. The combination of claim 2, wherein said penetration-resisting bearing surface extends at least 0.1 mm beyond a maximum radial extent of said shank.

4. The combination of claim 1, wherein said penetration-resisting bearing surface extends beyond a maximum radial extent of said cap.

5. The combination of claim 4, wherein said penetration-resisting bearing surface extends at least 0.1 mm beyond a maximum radial extent of said cap.

6. The combination of claim 1, wherein said penetration-resisting bearing surface is dimensioned to bear directly or indirectly against at least part of the tissue surrounding said opening during insertion of said plug into said meatus.

7. The combination of claim 1, wherein a portion of said penetration-resisting bearing surface indirectly bears against a portion of tissue surrounding said opening through said proximal cap of said plug, whereby said distal flange surface and said insertion-resisting bearing surface combine to form a substantially continuous combined surface.

8. The combination of claim 1, wherein a portion of said penetration-resisting bearing surface forms a barrier to axially proximal movement of said cap, whereby said penetration-resisting bearing surface and said proximal cap form a penetration-resisting functional unit.

9. The combination of claim 1, wherein said abutment is substantially cylindrical and wherein said penetration-resisting bearing surface is substantially circular having a diameter of between about 0.91 mm and about 6.0 mm.

10. The combination of claim 1, wherein said abutment comprises a plurality of angularly spaced apart surface portions having a cumulative area forming said penetration-resisting bearing surface.

11. The combination of claim 1, wherein said abutment comprises a pane of translucent material.

12. The combination of claim 1, which further comprises said distal portion of said tool having a lumen dimensioned to be intimately and slidingly engaged by said rod while limiting bending of said rod to a bend radius of greater than 0.35 meter.

13. The combination of claim 1, which further comprises said distal portion of said tool having a lumen dimensioned to be intimately and slidingly engaged by said rod, wherein said lumen has an internal diameter of between about 100.5 percent and about 300 percent of an outside diameter of said rod.

14. The combination of claim 1, which further comprises a rod tracking tube having an axial lumen dimensioned to be intimately and slidingly engaged by said rod wherein a difference between an outside diameter of said rod diameter and an inside diameter of said lumen diameter is less than about 2.0 mm.

15. A tool for inserting a punctal plug into the opening of a meatus, said tool comprises:
   a hand-graspable member;
   a rod extending distally from said member;
   said rod having a distal segment elongated along an axis, said distal segment having a free distal rod end; and,
   an abutment located an axial distance proximal from said distal rod end;
   wherein said abutment comprises:
   a radial prominence supporting an penetration-resisting bearing surface a radial distance from said distal segment;
   wherein said penetration-resisting bearing surface is shaped, dimensioned, and located to directly or indirectly bear against at least part of the tissue surrounding said opening during insertion of said plug into said meatus; and,
     at least one radial notch forming an angular discontinuity in said penetration-resisting bearing surface.

16. The tool of claim 15, wherein said penetration-resisting bearing surface is shaped and dimensioned to prevent over-penetration of said distal segment into said meatus.

17. The tool of claim 15, wherein said penetration-resisting bearing surface extends at least 0.1 mm beyond a maximum radial extent of the shank of the plug being inserted.

18. A method for seating a plug in the punctum of a patient, wherein said plug has a proximal cap having a distal flange surface for resting against the tissue surrounding the opening of said punctum, said method comprises:
   selecting an oblong inserter tool including a rod having a distal segment having a free distal rod end, and an abutment located an axial distance proximal from said distal rod end, said abutment supporting a penetration-resisting bearing surface having a radial dimension greater than a maximum radial dimension of said shank;
   releasably carrying a punctal plug on said distal rod end;
   pushing said plug axially through said punctum until said penetration-resisting bearing surface prevents further axial movement of said tool;
   viewing a portion of said tissue surrounding said opening through a gap in said penetration- resisting bearing surface;
   releasing said plug from said tool; and,
   axially pulling said tool away from said plug.

19. The method of claim 18, wherein the penetration-resisting bearing surface directly contacts a portion of the tissue surrounding said opening thereby preventing over-insertion of the rod and plug into the punctum and canaliculus.

20. The method of claim 18, wherein the penetration-resisting bearing surface indirectly contacts, through said cap, a portion of the tissue surrounding said opening thereby preventing over-insertion of the rod and plug into the punctum and canaliculus.

21. The method of claim 18, wherein said selecting further comprises:
   choosing an inserter tool so that said penetration-resisting bearing surface has a radial dimension which is at least 0.1 mm larger than the maximum radial dimension of the shank.

22. The method of claim 18, which further comprises:
   preventing bending of said rod to a bend radius of less than 0.35 meter during said pushing.

23. The method of claim 18, which further comprises:
   preventing bending of the rod;
   preventing inadvertent early retraction of the rod from the plug; and,
   preventing the plug from bending or falling off during insertion.

24. A method for seating a plug in the punctum of a patient, wherein said plug has a proximal cap having a distal flange surface for resting against the tissue surrounding the opening of said punctum, said method comprises:
   selecting an oblong inserter tool including a rod having a distal segment having a free distal rod end, and an abutment located an axial distance proximal from said distal rod end, said abutment supporting a penetration-resisting bearing surface having a radial dimension greater than a maximum radial dimension of said shank;
   releasably carrying a punctal plug on said distal rod end;
   pushing said plug axially through said punctum until said penetration-resisting bearing surface prevents further axial movement of said tool;
   viewing a portion of said tissue surrounding said opening through a pane of translucent material;
   releasing said plug from said tool; and, axially pulling said tool away from said plug.

25. The combination of a punctal plug and a tool for inserting said plug into the punctal opening of a meatus;
   wherein said plug comprises:
   a shank having a proximal end and a distal end;
   an insertable portion connected to said distal end; and,
   a proximal cap connected to said proximal end, said cap having a distal flange surface oriented to rest against at least part of the tissue surrounding said opening when said plug is properly emplaced in said meatus;
   wherein said tool comprises:
   a member having a distal portion, and a rod projecting from said distal portion;
   said rod having a distal segment elongated along an axis, said distal segment having a free distal rod end;

an abutment located an axial distance from said distal rod end;

wherein said abutment comprises:

a penetration-resisting bearing surface located at an axial position to resist penetration of said distal flange surface through said punctal opening, thereby preventing over-penetration of said plug into said meatus; and, a pane of translucent material.

26. A tool for inserting a punctal plug into the opening of a meatus, said tool comprises:

a hand-graspable member;

a rod extending distally from said member;

said rod having a distal segment elongated along an axis, said distal segment having a free distal rod end; and, an abutment located an axial distance proximal from said distal rod end;

wherein said abutment comprises:

a radial prominence supporting an penetration-resisting bearing surface a radial distance from said distal segment;

wherein said penetration-resisting bearing surface is shaped, dimensioned, and located to directly or indirectly bear against at least part of the tissue surrounding said opening during insertion of said plug into said meatus; and, a pane of translucent material.

* * * * *